(12) United States Patent
Siegal

(10) Patent No.: US 7,947,078 B2
(45) Date of Patent: May 24, 2011

(54) DEVICES FOR FORMING CURVED OR CLOSED-LOOP STRUCTURES

(75) Inventor: Tzony Siegal, Moshav Shoeva (IL)

(73) Assignee: NonLinear Technologies Ltd., Ariel (IL)

( * ) Notice: Subject to any disclaimer, the term of this patent is extended or adjusted under 35 U.S.C. 154(b) by 219 days.

(21) Appl. No.: 12/521,585

(22) PCT Filed: Jan. 9, 2008

(86) PCT No.: PCT/IL2008/000043
§ 371 (c)(1),
(2), (4) Date: Jun. 29, 2009

(87) PCT Pub. No.: WO2008/084479
PCT Pub. Date: Jul. 17, 2008

(65) Prior Publication Data
US 2011/0093072 A1 Apr. 21, 2011

Related U.S. Application Data

(60) Provisional application No. 60/884,022, filed on Jan. 9, 2007, provisional application No. 60/947,426, filed on Jul. 1, 2007.

(51) Int. Cl.
*A61B 17/70* (2006.01)
*A61F 2/44* (2006.01)

(52) U.S. Cl. ............... 623/17.11; 606/246; 606/279; 606/90; 606/92; 59/78.1; 248/49; 248/51; 623/17.15

(58) Field of Classification Search ........... 623/17.11, 623/17.12, 17.15; 606/90, 92, 105, 170, 606/246, 279; 59/78, 78.1, 84
See application file for complete search history.

(56) References Cited

U.S. PATENT DOCUMENTS

| | | | | | |
|---|---|---|---|---|---|
| 3,930,587 | A | * | 1/1976 | Bliss | 414/664 |
| 4,312,337 | A | * | 1/1982 | Donohue | 606/80 |
| 4,941,466 | A | * | 7/1990 | Romano | 606/80 |
| 5,322,505 | A | * | 6/1994 | Krause et al. | 604/24 |
| 5,695,513 | A | * | 12/1997 | Johnson et al. | 606/180 |
| 5,836,148 | A | * | 11/1998 | Fukao | 59/78.1 |
| 5,970,701 | A | * | 10/1999 | Roden et al. | 59/78 |
| 6,387,002 | B1 | * | 5/2002 | Gunter | 474/206 |
| 7,344,564 | B2 | * | 3/2008 | Sweeney | 623/17.15 |
| 7,666,226 | B2 | * | 2/2010 | Schaller | 623/17.11 |
| 7,673,440 | B2 | * | 3/2010 | Blase et al. | 59/78.1 |

(Continued)

FOREIGN PATENT DOCUMENTS
DE 19710392 C1 * 7/1999
(Continued)

*Primary Examiner* — David B Jones
(74) *Attorney, Agent, or Firm* — Mark M. Friedman

(57) ABSTRACT

A device for forming structurally stable curved structures includes an elongated element (10) with a number of segments (12) interconnected at effective hinges (14) to allow deflection of each segment relative to adjacent segments between a reduced-curvature state and a flexed state. Neighboring segments have interlocking features (16) forming an inter-segment locking configuration such that, when the segments are deflected from the reduced-curvature state to the flexed state, the interlocking features interlock adjacent of the segments so as to retain the segments in the flexed state corresponding to a predefined curved configuration of the elongated element. Additionally, or alternatively, a leading portion (44) and a rear portion (40) of the elongated element have features forming at least part of a loop-lock configuration effective to lock together the leading portion and the rear portion so as to form a closed loop structure.

14 Claims, 36 Drawing Sheets

U.S. PATENT DOCUMENTS

2005/0060036 A1* 3/2005 Schultz et al. ............. 623/17.15
2005/0273166 A1* 12/2005 Sweeney .................... 623/17.11
2006/0142858 A1* 6/2006 Colleran et al. ........... 623/17.11
2008/0208255 A1* 8/2008 Siegal .......................... 606/246

FOREIGN PATENT DOCUMENTS

| DE | 20 2006 005 868 U1 | * | 7/2006 |
| WO | WO 2005/094368 | * | 10/2005 |
| WO | WO 2007/022194 A2 | * | 2/2007 |

* cited by examiner

DEVICES FOR FORMING CURVED OR CLOSED-LOOP STRUCTURES

RELATED APPLICATIONS

This patent application is a National Stage of PCT/IL2008/000043 filed on Jan. 9, 2008, which claims the benefit under 119(e) of U.S. Provisional Patent Application No. 60/884,022 filed Jan, 9, 2007, and U.S. Provisional Patent Application No. 60/947,426 filed Jul. 1, 2007 the contents of which are incorporated herein by reference.

FIELD AND BACKGROUND OF THE INVENTION

The present invention relates to a device for forming curved structures. PCT patent application publication no. WO 2006/072941 teaches a wide range of devices and corresponding applications in which an elongated element is introduce into a body in a straightened configuration and then assumes a curved or coiled configuration within the body. The aforementioned publication is hereby incorporated by reference herein in its entirety, and will be referred to below as the '941 publication.

In certain applications, it would be advantageous to provide additional mechanical stability to the curved or coiled structures of the aforementioned publication or to provide a stable closed-loop structure.

SUMMARY OF THE INVENTION

The present invention is a device for forming structurally stable curved structures and/or closed loops.

According to the teachings of the present invention there is provided, a device for fowling structurally stable curved structures comprising an elongated element formed from a plurality of segments sequentially interconnected so as to form an effective hinge between adjacent of the segments, the segments and the effective hinges being configured such that the effective hinges allow deflection of each segment relative to adjacent segments between a reduced-curvature state and a flexed state, wherein adjacent of the segments are provided with interlocking features together forming an inter-segment locking configuration such that, when the segments are deflected from the reduced-curvature state to the flexed state, the interlocking features interlock adjacent of the segments so as to retain the segments in the flexed state corresponding to a predefined curved configuration of the elongated element.

According to a further feature of the present invention, According to a further feature of the present invention, the interlocking features include a projecting spring element projecting from each of a plurality of the segments and deployed for interlocking engagement with a cooperating recess in adjacent of the segments.

According to a further feature of the present invention, the projecting spring element is integrally formed with each of the plurality of segments.

According to a further feature of the present invention, each of the effective hinges is formed by a flat connecting portion of flexible material interconnecting between adjacent of the segments.

According to a further feature of the present invention, each of the flat connecting portions is integrally formed with adjacent of the segments.

According to a further feature of the present invention, all of the segments and the flat connecting portions are integrally formed.

According to a further feature of the present invention, each of the flat connecting portions is resiliently biased to deflect the segments to the flexed state so that the elongated element tends to assume the predefined curved configuration.

According to a further feature of the present invention, each of the segments is formed as a non-hollow block of material.

According to a further feature of the present invention, each of the segments is formed as a hollow block of material.

According to a further feature of the present invention, the elongated element further includes a beveled distal tip angled so as to tend to deflect the elongated element into the fully flexed state as the elongated element advances through a medium.

According to a further feature of the present invention, there are also provided at least one fixation arrangement for fixing a part of the elongated element relative to a body such that the elongated element forms at least part of an implant.

According to a further feature of the present invention, a length of the elongated element is at least ten times greater than each transverse dimension of the elongated element.

According to a further feature of the present invention, the predefined curved configuration includes a helix.

According to a further feature of the present invention, lateral surfaces of the segments are formed with complementary interlocking features so as to inhibit lateral displacement of successive coils of the helix.

According to a further feature of the present invention, there is also provided a delivery conduit having a passageway shaped to allow delivery of the elongated element along the passageway, the delivery conduit including deflecting features arranged so as to force adjacent of the segments into the flexed state as the elongated element is advanced through the delivery conduit, thereby forming the predefined curved configuration in a portion of the elongated element emerging from the delivery conduit.

According to a further feature of the present invention, a leading portion and a rear portion of the elongated element include features forming at least part of a loop-lock configuration, the loop-lock configuration being operative to lock together the leading portion and the rear portion so as to form a closed loop structure.

There is also provided according to the teachings of the present invention, a device for forming closed loop structures comprising an elongated element formed from a plurality of segments sequentially interconnected so as to fowl an effective hinge between adjacent of the segments, the segments and the effective hinges being configured such that the effective hinges allow deflection of each segment relative to adjacent segments between a reduced-curvature state and a flexed state, wherein a leading portion and a rear portion of the elongated element include features fowling at least part of a loop-lock configuration, the loop-lock configuration being operative to lock together the leading portion and the rear portion so as to form a closed loop structure.

According to a further feature of the present invention, the rear portion of the elongated element includes a cavity for receiving at least part of the leading portion.

According to a further feature of the present invention, the leading portion has a first width measured parallel to the effective hinge and the rear portion has a second width measured parallel to the effective hinge, the second width being greater than the first width.

According to a further feature of the present invention, the leading portion is configured to engage an edge of the cavity.

According to a further feature of the present invention, the leading portion includes a shaped recess for engagement by a locking element.

According to a further feature of the present invention, the loop-lock configuration further includes an elongated locking element for engaging the shaped recess, and wherein the rear portion is formed with a bore for receiving the elongated locking element.

According to a further feature of the present invention, the elongated locking element and the bore are threaded.

According to a further feature of the present invention, the bore is a rearward-opening bore.

According to a further feature of the present invention, each of the effective hinges is formed by a flat connecting portion of flexible material interconnecting between adjacent of the segments.

According to a further feature of the present invention, each of the flat connecting portions is integrally formed with adjacent of the segments.

According to a further feature of the present invention, all of the segments and the flat connecting portions are integrally formed.

According to a further feature of the present invention, there is also provided a delivery conduit having a passageway shaped to allow delivery of the elongated element along the passageway, the conduit including a lateral opening for accommodating at least part of the leading portion.

According to a further feature of the present invention, the conduit includes at least one feature configured to engage part of the leading portion, thereby providing part of the loop-lock configuration.

There is also provided according to the teachings of the present invention, a device for forming closed loop structures comprising: (a) an elongated element formed from a plurality of segments sequentially interconnected so as to form an effective hinge between adjacent of the segments, the segments and the effective hinges being configured such that the effective hinges allow deflection of each segment relative to adjacent segments between a reduced-curvature state and a flexed state; and (b) a delivery conduit having a passageway shaped to allow delivery of the elongated element along the passageway, the delivery conduit being configured to remain interconnected with a rear portion of the elongate element, wherein a leading portion of the elongated element and the delivery conduit include features forming at least part of a loop-lock configuration, the loop-lock configuration being operative to lock together the leading portion and the conduit so as to faun a closed loop structure.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
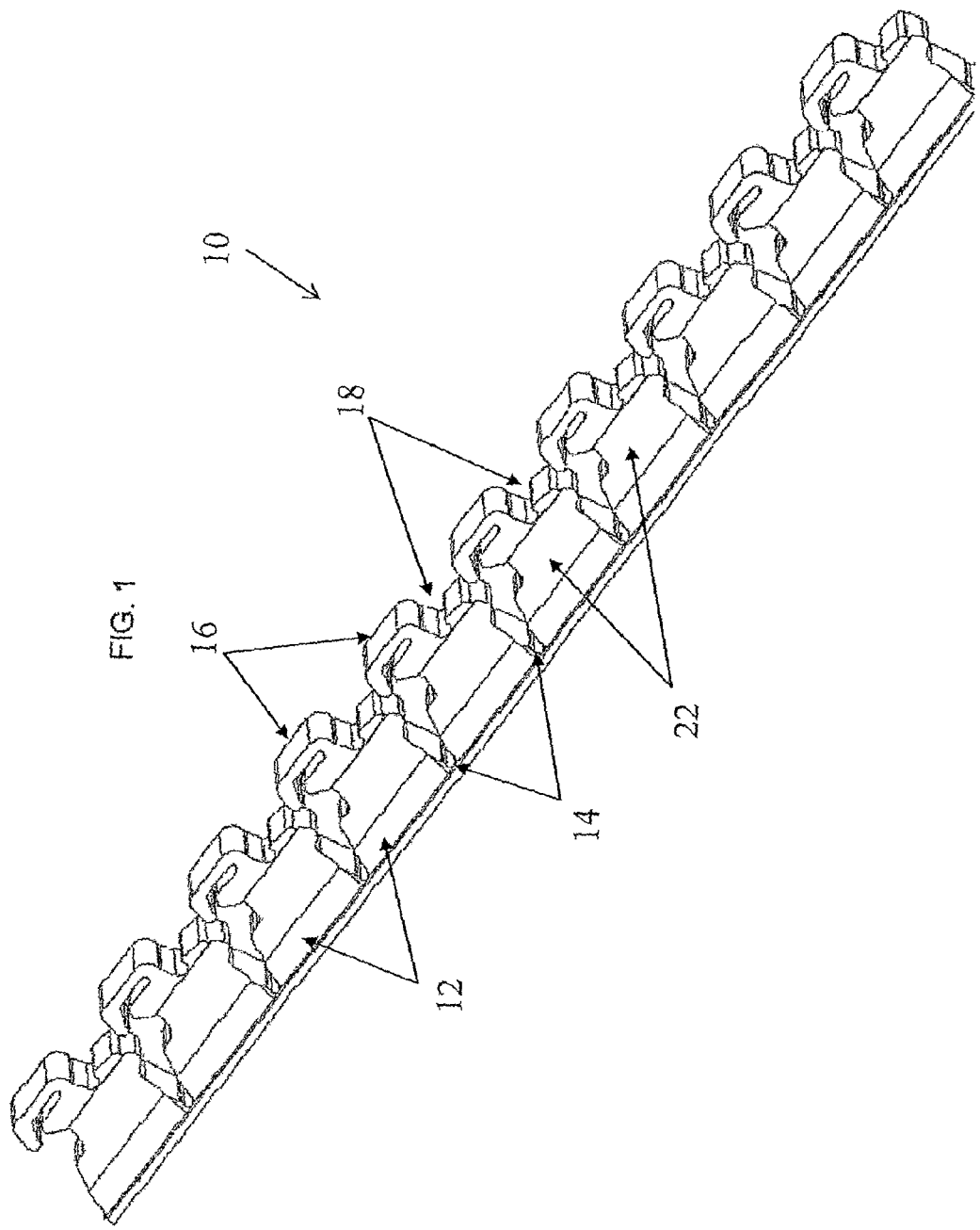
FIGS. 1-4 are various isometric views of an elongated element of a first preferred embodiment of the present invention, shown in its straightened, delivery configuration with the inter-segment locking configurations unlocked.
Figure 2:
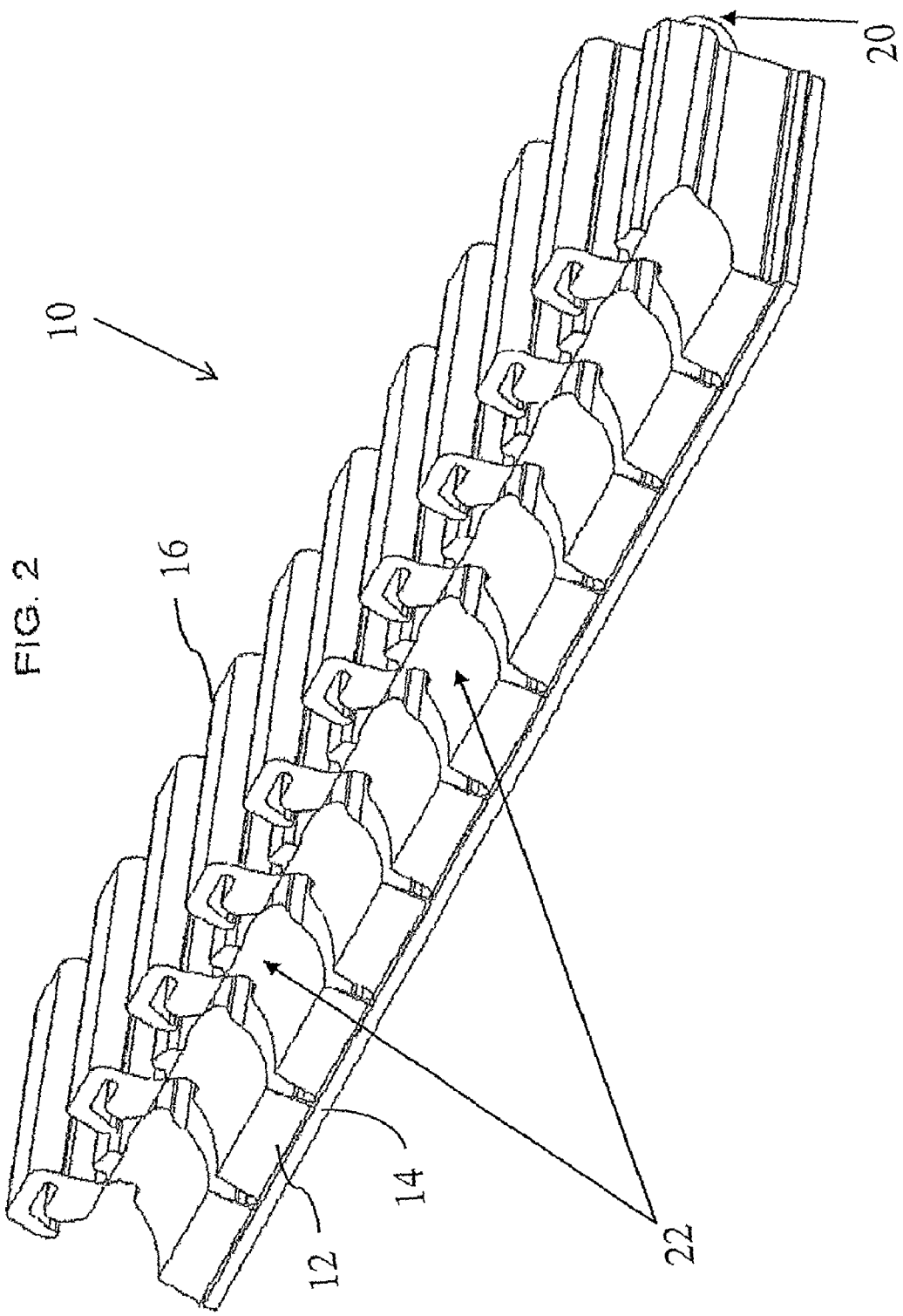
Figure 3:
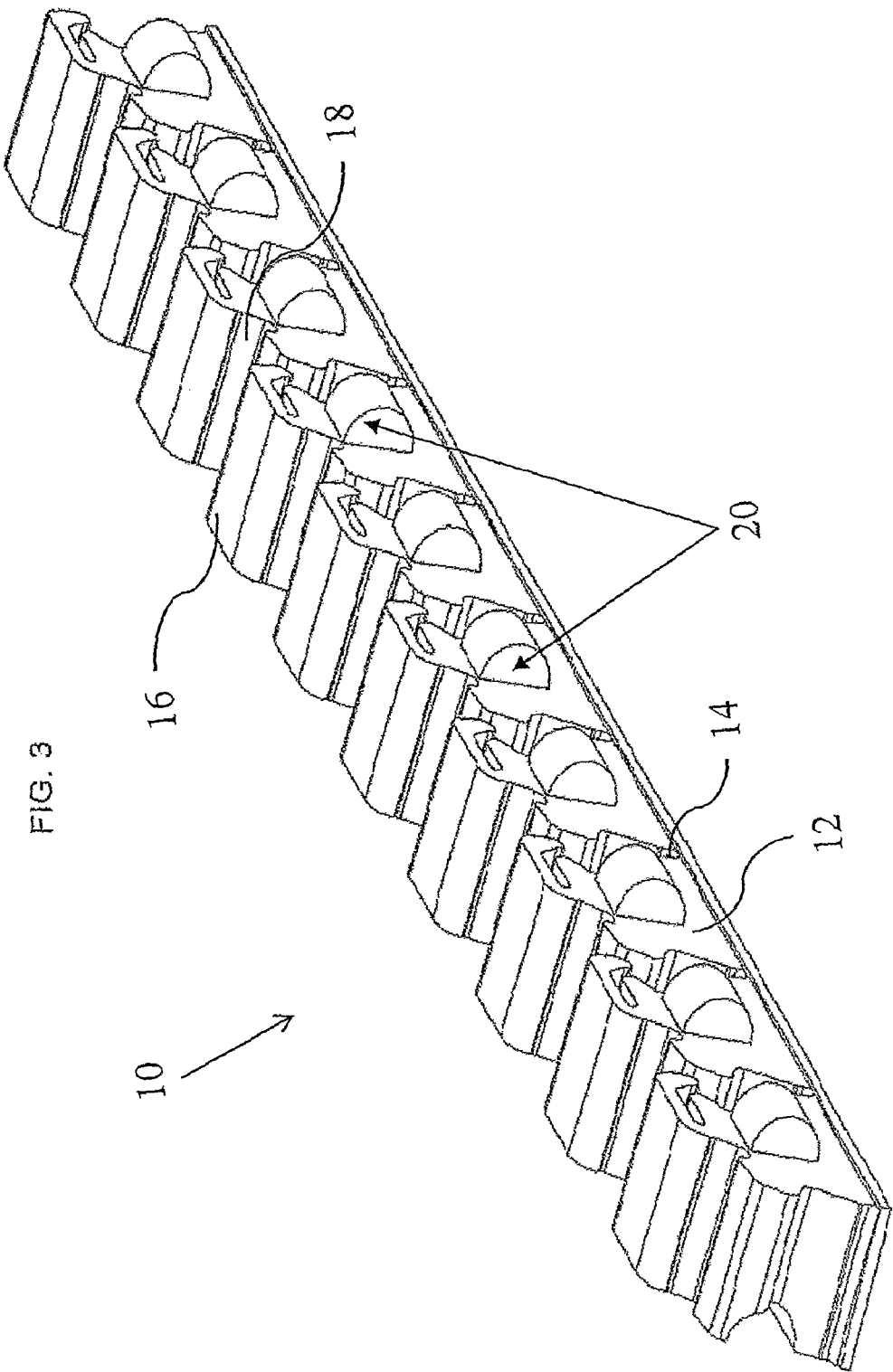
Figure 4:
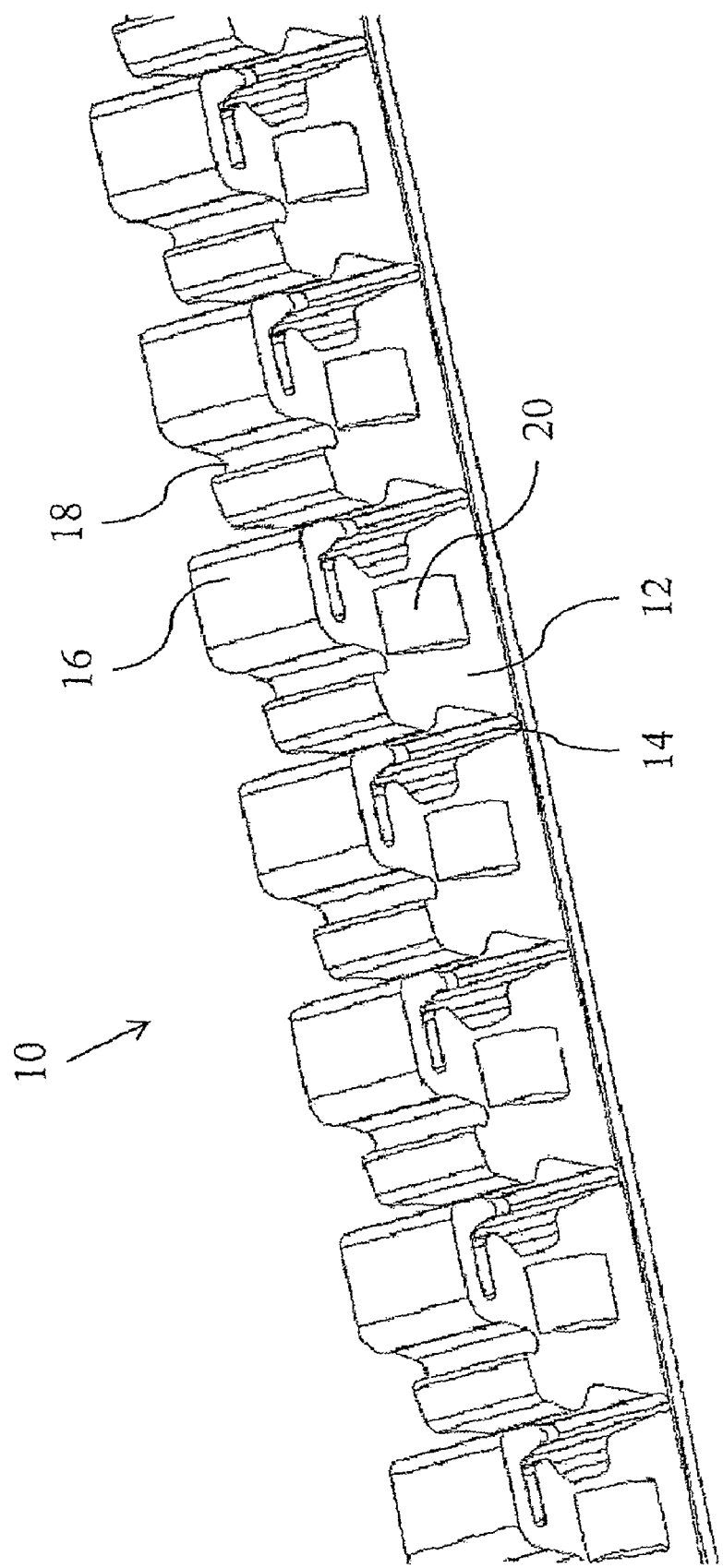
Figure 5:
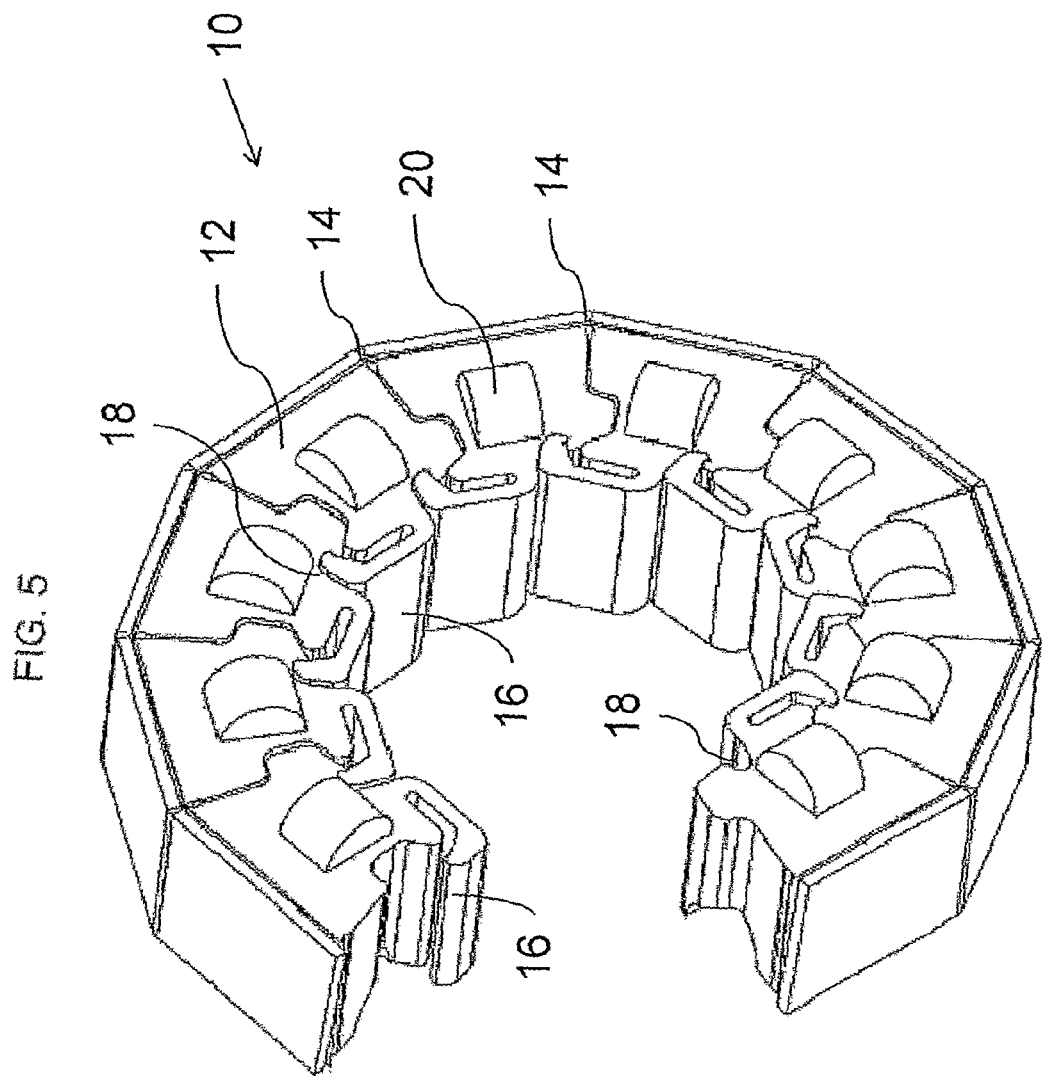
FIGS. 5-8 are various isometric views of the elongated element of FIGS. 1-4 shown in its curved state with the inter-segment locking configurations locking between adjacent segments.

The present invention is a device for forming structurally stable curved structures and/or closed loops. The invention also provides methods for introducing such curved structures and loops into a body.

The principles and operation of devices and methods according to the present invention may be better understood with reference to the drawings and the accompanying description, and with reference to the aforementioned PCT patent application publication no. WO 2006/072941 ("the '941 publication"), which is incorporated by reference herein. Except where specified otherwise, it should be assumed that the structure and function of the present invention, as well as the range of possible applications, details of materials and all other information are as described in the '941 publication.

By way of introduction, the present invention relates primarily to a class of devices similar to those described in the '941 publication, namely, where an elongated element is introduced into a body in a straightened or low-curvature configuration and then assumes within the body a predefined curved configuration. The elongated element is formed at least in part from a plurality of segments sequentially interconnected so as to form an effective hinge between adjacent of the segments.

The present invention differs primarily from the devices disclosed in the '941 publication by the presence of one or more of a number of preferred features. Specifically, according to a first set of additional features, the devices of the present invention provide an inter-segment locking configuration between at least some and preferably all pairs of adjacent segments configured to lock the relative positions of adjacent segments into their predefined curved configuration. This inter-segment locking configuration provides a high degree of structural stability and ensures a well defined deployed configuration in which the segments do not accidentally open towards their straightened insertion configuration.

According to a second additional, or alternative, set of features, the present invention provides a loop-lock configuration for anchoring the tip of the elongated element in relation to the following part of the element to faun a structurally stable closed loop. Optionally, a part of the guide or conduit through which the elongated element is deployed may form part of the loop-lock configuration. The loop-lock configuration may be used to advantage together with the inter-segment locking configuration to provide a particularly stable and strong ring-like structure useful in a wide range of applications.

In an alternative set of preferred embodiments, the inter-segment locking configuration is used in combination with helical configurations such as those of FIGS. 10, 13, 14, 17A and 17B of the '941 publication. In the case of close-coiled helices, which form roughly cylindrical deployed structures, the segments may advantageously include lateral projections and corresponding recesses to help maintain accurate superposition of successive coils of the helix.

An additional preferred feature of the present invention is provision of a delivery conduit with a terminal portion configured to ensure that a predetermined minimum curvature is achieved for the elongated element as it leaves the delivery conduit. In the case of configurations having the inter-segment locking configuration of the present invention, the conduit preferably ensures that the adjacent segments are locked into their deflected state as they are deployed. In certain cases, the conduit also performs the reverse function, allowing for mechanical opening of the locking configuration and straightening of the elongated element in the case that the element is subsequently withdrawn via the conduit. These and other features of the present invention will be better understood from the following detailed description.

Referring now to the drawings, FIGS. 1-4 show a first embodiment of the elongated element, constructed and operative according to the teachings of the present invention, in its straightened state ready for delivery, and FIGS. 5-8 show the same element in its helical state. It will be noted that the length of the element may be varied according to the desired application, and is typically longer than the single loop illustrated in some of these drawings. In most cases, the length of the elongated element is at least ten times greater than each of the transverse dimensions of the elongated element.

In general terms, this and other embodiments of the present invention include an elongated element 10 faulted from a plurality of segments 12 sequentially interconnected so as to form an effective hinge 14 between adjacent segments. Segments 12 and effective hinges 14 are configured such that effective hinges 14 allow deflection of each segment relative to adjacent segments between a reduced-curvature (typically straight or near-straight) state as shown in FIGS. 1-4 and a flexed state as shown in FIGS. 5-8.

Effective hinges 14 are preferably formed by a flat connecting portion of flexible material interconnecting between adjacent of the segments. This flat connecting portions is preferably integrally formed with the adjacent segments 12. Most preferably, all of segments 12 and the flat connecting portions are integrally formed. For machinable materials, the element can thus be produced by selective removal of material from an initial block or tube. For moldable materials, the element can thus be fowled by injection molding as a single body. Depending on the desired properties for a given application, the effective hinges may be formed with an initial resilient bias to any particular desired state, such as for example a resilient bias towards the flexed state so that the elongated element tends to assume the predefined curved configuration.

It is a particular feature of devices according to this aspect of the present invention that adjacent of segments 12 are provided with interlocking features together forming an inter-segment locking configuration such that, when the segments are deflected from the reduced-curvature state to the flexed state, the interlocking features interlock adjacent of segments 12 so as to retain segments 12 in the flexed state corresponding to a predefined curved configuration of the elongated element. In the preferred embodiment illustrated here, the interlocking features include a projecting spring element 16 projecting from each segment 12 and deployed for interlocking engagement with a cooperating recess 18 in an adjacent segment 12. Most preferably, projecting spring element 16 is integrally formed with the corresponding segment 12. The desired degree of flexibility is ensured by choosing a thickness of the material in accordance with the properties of the material from which the segments are made. Projecting spring element 16 may extend forward for engaging a cooperating recess in the preceding (leading) segment, may extend backwards to engaging a cooperating recess in the following segment. Optionally, projecting spring elements 16 on one or more segments may extend in both directions to engage recesses in two adjacent segments, and some segments may be implemented with recesses only.

As already mentioned, the present invention can be used in a wide range of fields of application including, but not limited to, building, mining, industrial applications, carpentry, and medicine. Accordingly, the "body" within which the device is deployed may be any body, including but not limited to: a human body; an animal body; wood; other biological materials; walls; furniture; minerals; and other inanimate objects. Clearly, the dimensions, materials and other design parameters for the device of the present invention are selected to render it suited to the intended application, as will be clear to one ordinarily skilled in the field of applications for which it is to be used.

It will be appreciated that the structure shown provides all the structural features of the device of the present invention in a very straightforward and easily manufactured manner, simply by forming appropriately shaped and positioned slots in a rod, or by molding techniques, depending on the material used. Effective hinges 14 are thus integrally formed as flat connecting portions of flexible material interconnecting between adjacent segments. The term "flat" is used in this context to refer to the cross-sectional shape, namely, that in cross-section along the effective axis of the hinge, the thickness of the integral hinge is significantly less than its width, thereby providing a well-defined direction of flexing. The integral hinge may have significant length extending between segments 12 or may have minimal length (such as illustrated here). Effective hinges 14 preferably provide resistance to relative motion of adjacent segments 12 other than the intended hinged motion, thereby avoiding unwanted torsional deformation of elongated element 10.

Clearly, if the device is constructed by cutting slots in an initially straight rod of material, and unless the elongated element is further treated to change its properties, the unstressed state of the elongated element will be in the straightened configuration. According to a particularly preferred option illustrated here, elongated element 10 terminates in a beveled distal tip (not shown here, but similar to that illustrated in FIG. 16, below) angled so as to tend to deflect the elongated element into the fully flexed state as the elongated element advances through a medium. Specifically, the beveled distal tip preferably has a leading edge on the side from which the slots are cut and a bevel surface facing away from the side of slots. This shape, when advanced into a compressible or displaceable medium, tends to be deflected so as to follow a curved path, thereby bending elongated element 10 progressively towards its fully flexed curved form as it advances beyond delivery conduit 20.

The dimensions of the device of the present invention are chosen according to the intended application and the required predefined curved shape which is to be formed. Thus, at one extreme, for use in hollowing out a subterranean tunnel or an underwater tunnel, an element with a width and height of one meter or more may be used. At the other extreme, certain delicate medical applications may use an elongated element with a width and height of 5 millimeters or less. For a wide range of domestic and medical applications, lateral dimensions of 1-30 mm are suitable.

In terms of relative dimensions, elongated element 10 is termed "elongated" in the sense that its length is significantly longer than both its width and its height. Most preferably, a length of elongated element 10 is at least ten times greater than each transverse dimension (height and width) of the elongated element. Preferably, the device is configured to form a predefined curved configuration including an arc turning through an angle of at least 180°, and in many cases, passing through one or more complete revolutions as will be illustrated in a number of examples below.

The materials for the device of the present invention are also chosen according to the intended application and the mechanical and other properties which are required, and may be any suitable materials. For many applications, various metals and metal alloys (referred to collectively as metallic materials) are suitable. For some applications, various plastics and other polymer materials are suitable. Other possibilities include, but are not limited to, composite materials and ceramic materials. For medical applications, biocompatible are used, typically either metallic materials or polymers such as PEEK. Where the device is intended to function as an implant, at least one fixation arrangement is provided, for example, a hole for insertion of a bone screw (not shown) for fixing a part of the elongated element relative to the body.

Turning back now to features of the inter-segment locking configurations in more detail, by suitable choice of the shape of the notch or recess 18 the shape of the complementary part of the spring element and the resilient properties of the spring element, it is possible to determine the resistance of the locking configuration to subsequent re-opening, as well as a desired degree of rigidity or flexibility in the locked state. For example, if the spring element is formed with a relatively flexible body but the engaging portions of the spring element and the recess are formed with steep edges that resist disengagement, the locked arcuate state may provide significant flexibility (e.g., ability to resiliently vary the diameter of the coils) while retaining structural integrity. On the other hand, an example with a relatively strong/stiff spring may provide a more rigid (i.e., fixed geometry) deployed state.

It will be noted that the locking configuration is preferably located on the far side of the segments from the hinged interconnection 14. In other words, if hinged interconnection 14 is at or near the outer extremity of the deployed curved form illustrated in FIGS. 5 and 6, the locking configuration is most preferably at or near the radially innermost part of the segments. Once engaged, the combination of the locking mechanism together with the hinged interconnection thus provides a high degree of structural stability. Nevertheless, it should be appreciated that other positions of the locking configuration, and of the hinged interconnection between the segments, also fall within the scope of the present invention.

Figure 6:
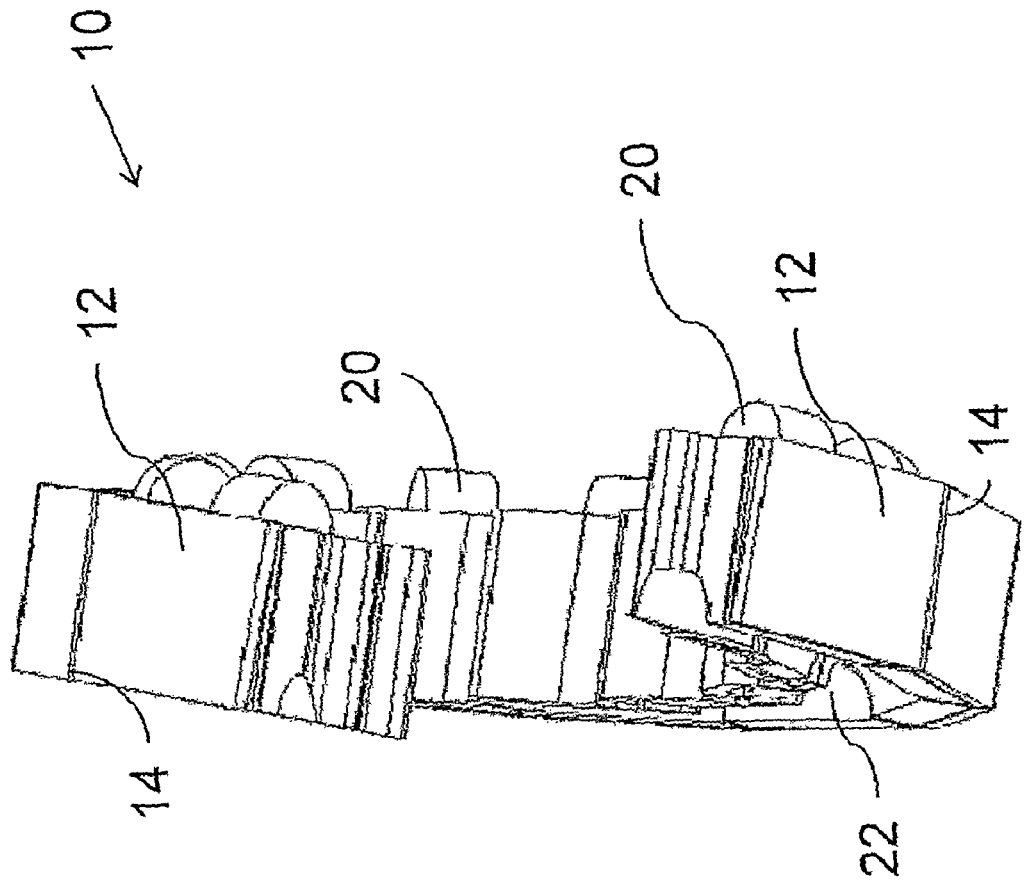
Figure 7:
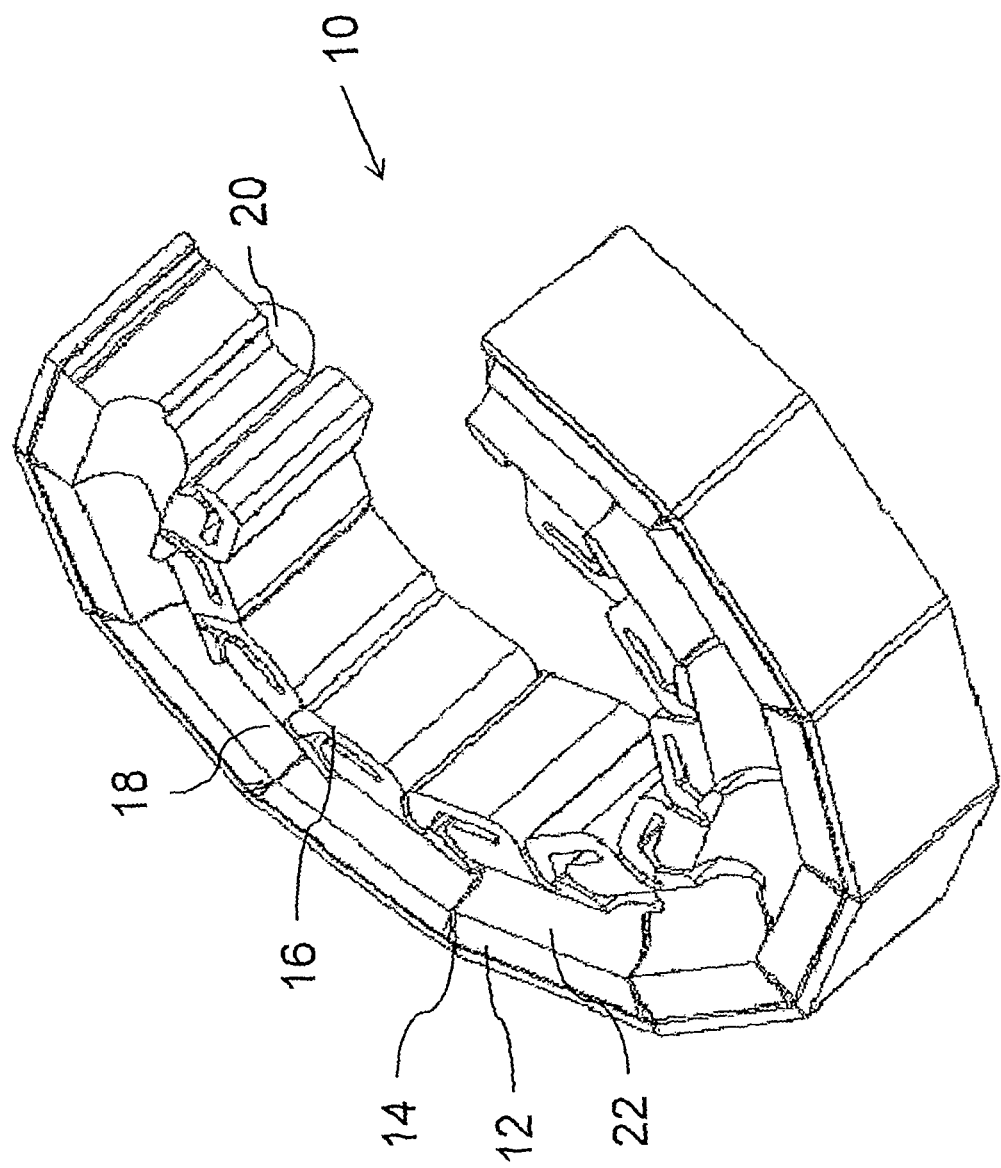
Figure 8:
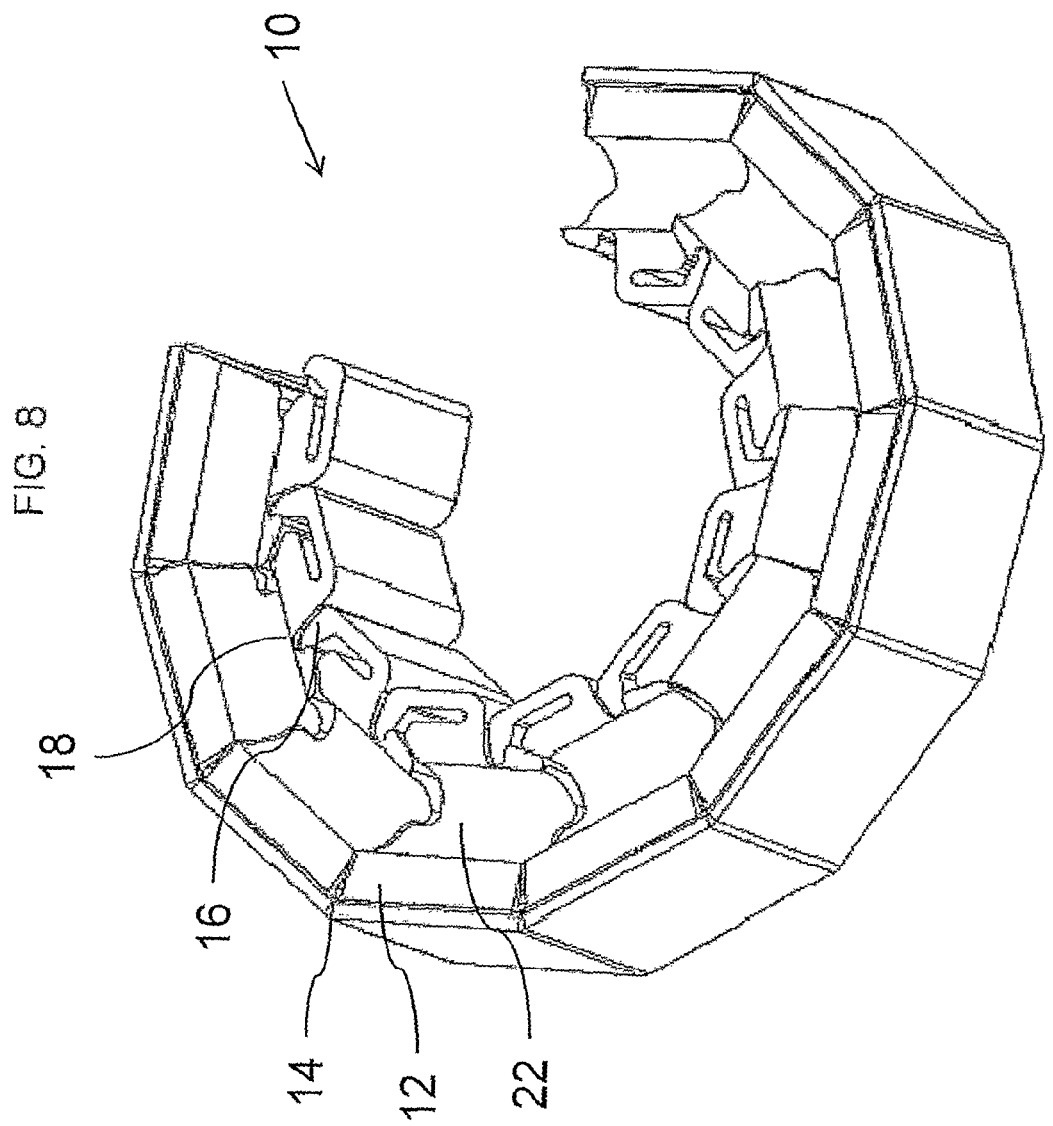

As particularly clear in FIG. 6, this example of the invention has a predefined curved configuration which is axially progressive so as to form a helix (when extended more than one turn). In order to stabilize the coils of the resulting helix, lateral surfaces of segments 12 are preferably formed with complementary interlocking features so as to inhibit lateral displacement of successive coils of the helix. Specifically, one side of segments 12 feature lateral projections 20 while the other side features recesses 22 to help maintain alignment of successive coils one upon another. In the case shown here, the projections and recesses are substantially cylindrical in shape. Other shapes, such as triangular wedge shapes etc. may also be used. These shapes provide a self-aligning or self-centering property for centering the projection within the recess.

Figure 9:
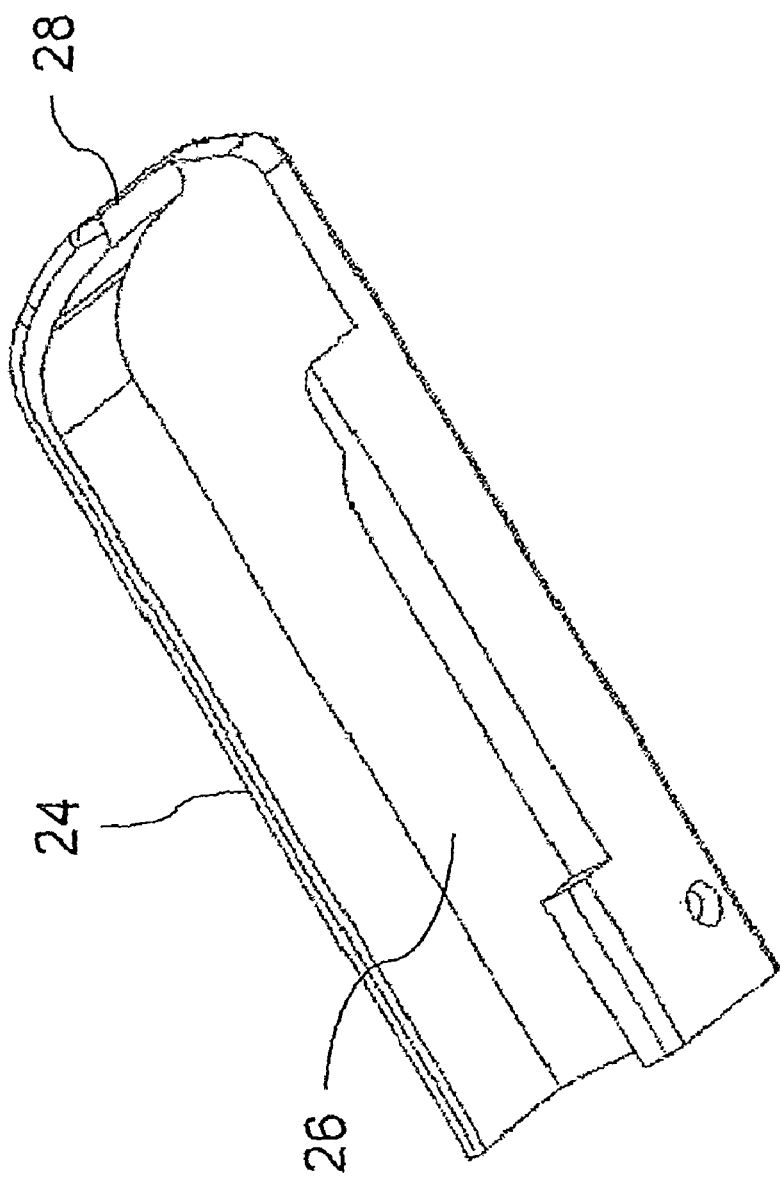
FIGS. 9-11 are various isometric views of a terminal portion of a delivery conduit, constructed and operative according to the teachings of the present invention, for use with the elongated element of FIGS. 1-8.
Figure 10:
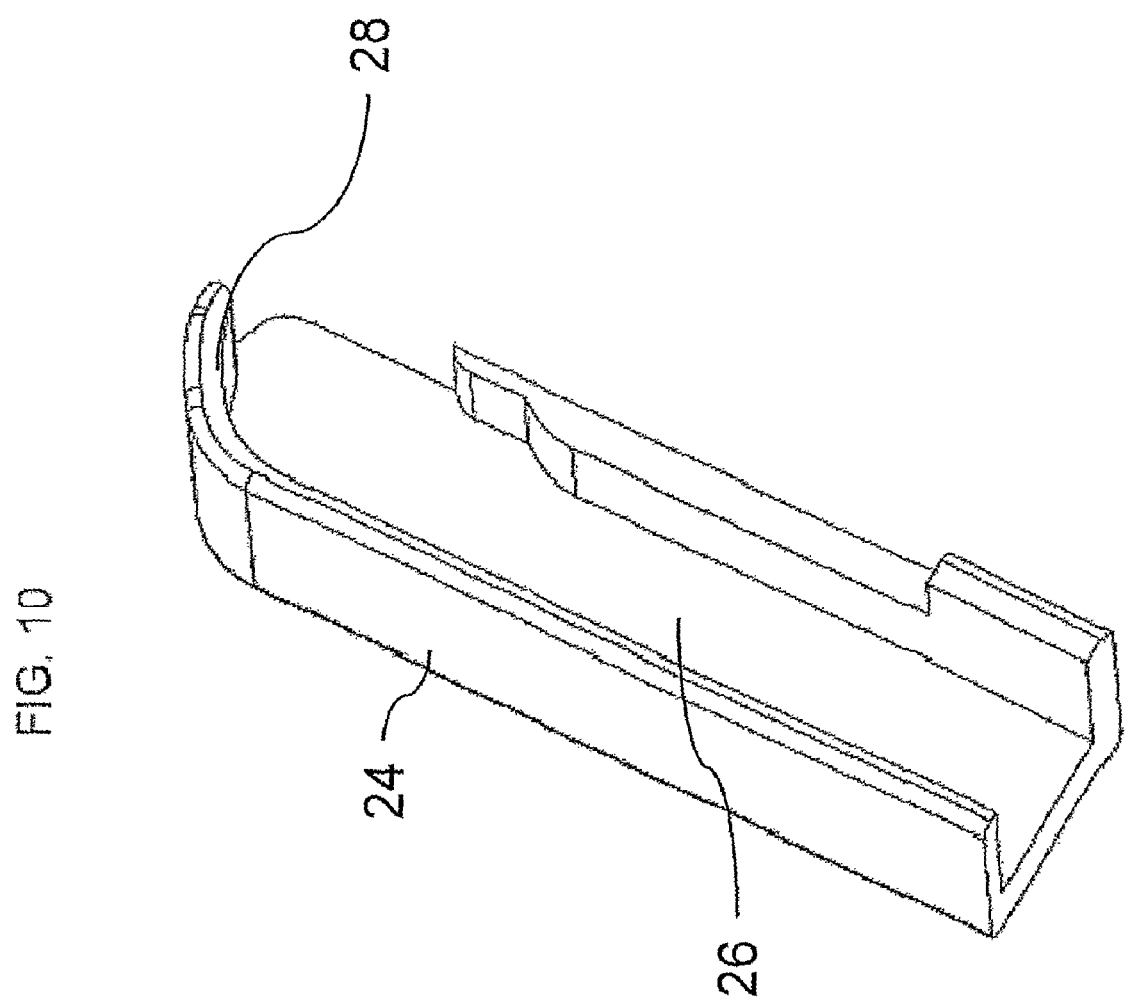
Figure 11:
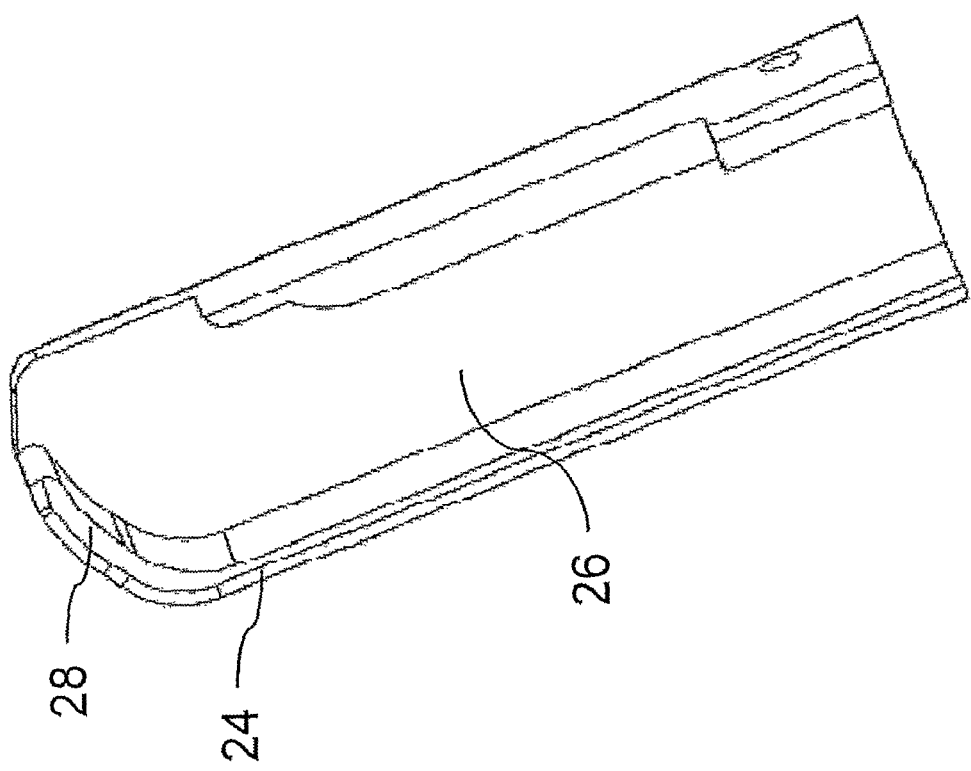
Figure 12:
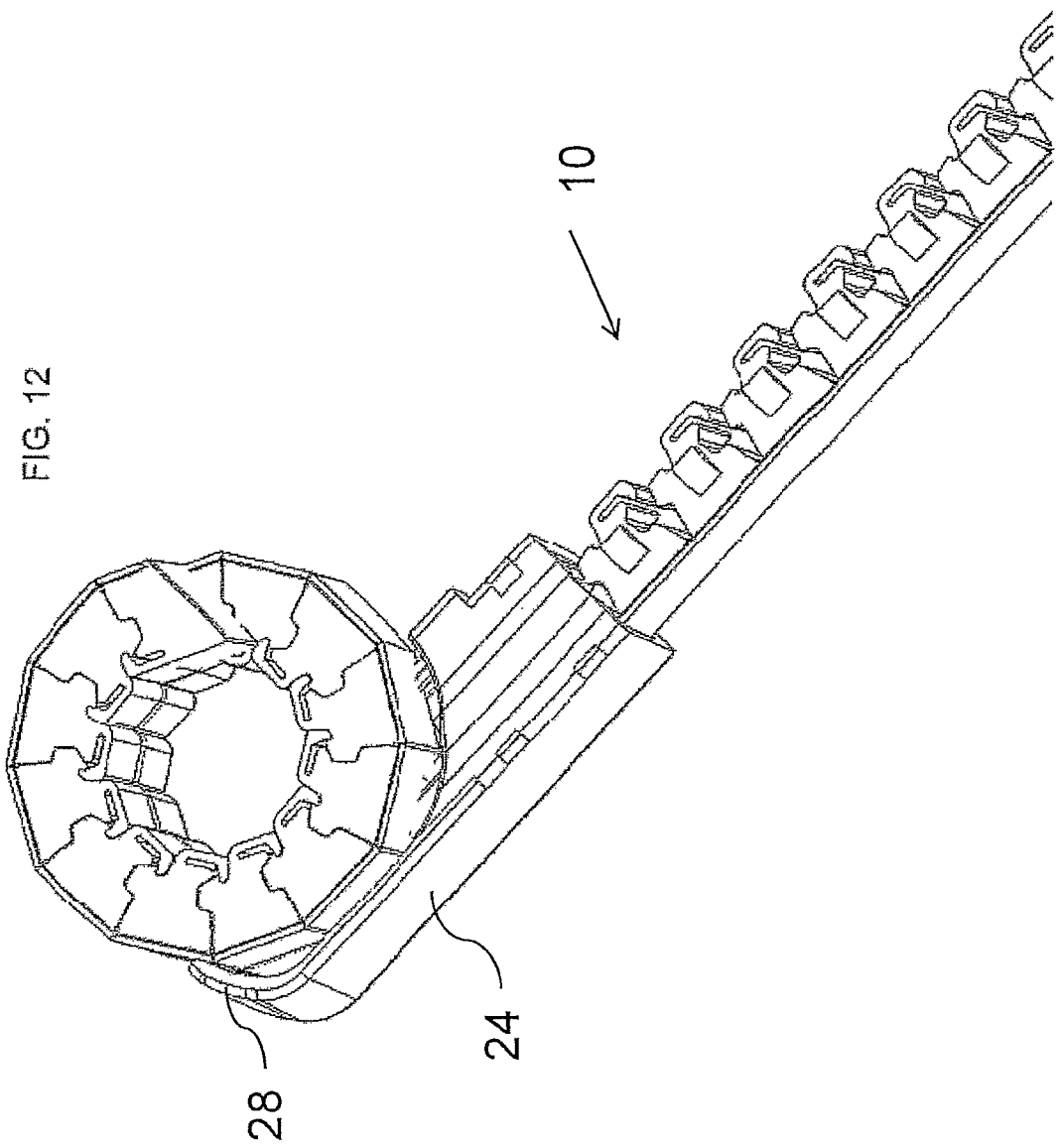
FIGS. 12 and 13 are isometric views of a device, constructed and operative according to the teachings of the present invention, showing deployment of the elongated element of FIGS. 1-8 from the delivery conduit of FIGS. 9-11.
Figure 13:
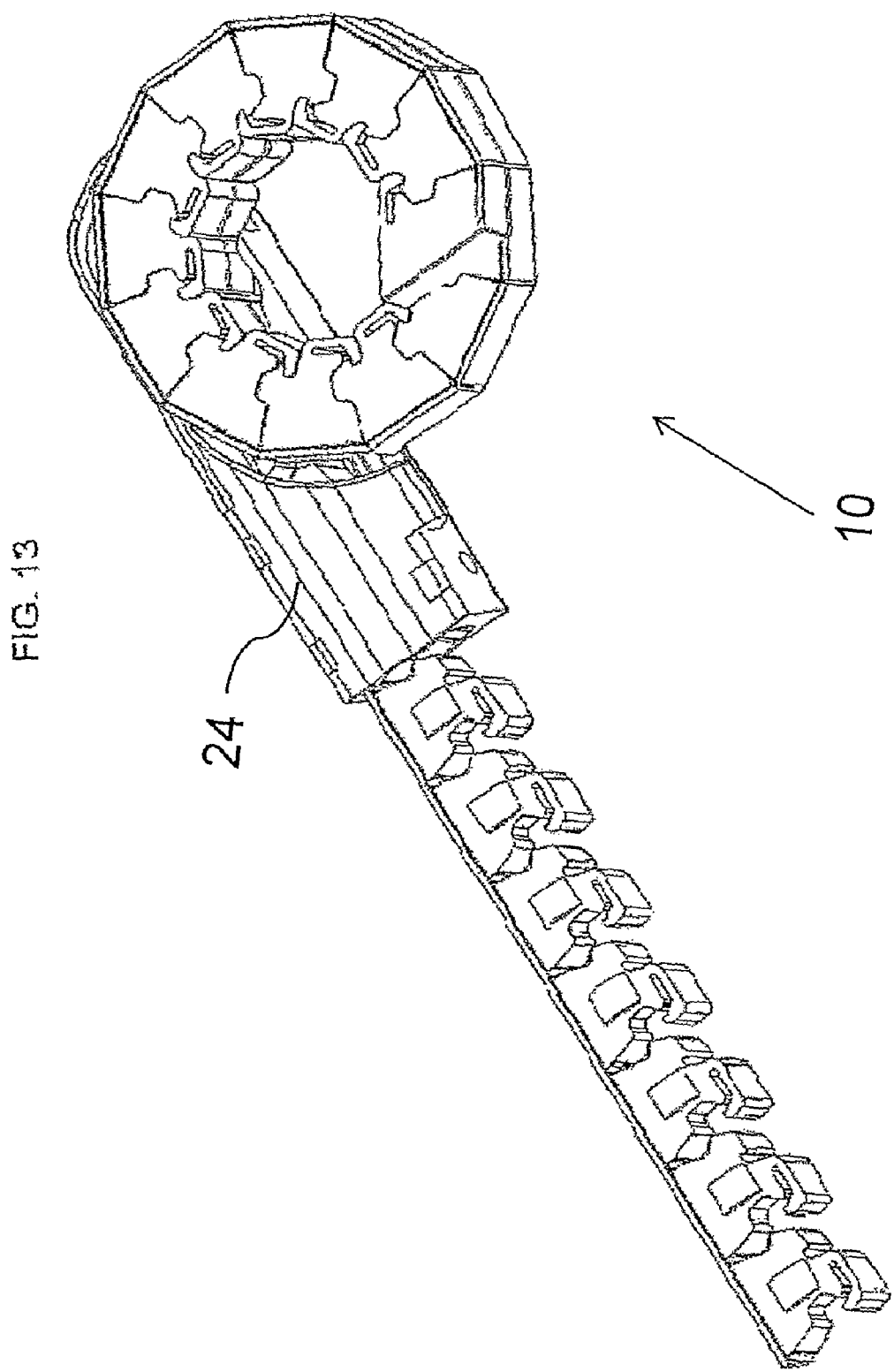

Turning now to FIGS. 9-11, there is shown a delivery conduit 24 having a passageway 26 shaped to allow delivery of elongated element 10 along the passageway. Delivery conduit 24 preferably has deflecting features arranged so as to force adjacent segments 12 into the flexed state as elongated element 10 is advanced through delivery conduit 24, thereby forming the predefined curved configuration in a portion of elongated element 10 emerging from delivery conduit 24. The deflecting features here include an inclined deflecting wall 28 that ensures that each segment is deflected relative to the previous segment prior to leaving the delivery conduit. The operation of the delivery conduit 24 is illustrated in FIGS. 12 and 13 where can be seen that a closed-coil helix forms, extending progressively laterally from the terminal portion of delivery conduit 24 as elongated element 10 is advanced. In order to avoid obstructing successive coils of the closed-coil helix, delivery conduit 24 preferably has a suitably-shaped lateral cut-out on the side to which the coils are to be deployed. The diameter and pitch of the helical form are determined by the geometrical parameters of the segments and the angular inclination of the pivotal interconnection between adjacent segments, all as detailed in the '941 publication. Also as detailed therein, it should be noted that the diameter and pitch may vary along the length of the element, and that other more complex forms may be made. In such cases, the dimensions and other parameters of the locking configuration may vary along the length of the elongated element.

Figure 14:
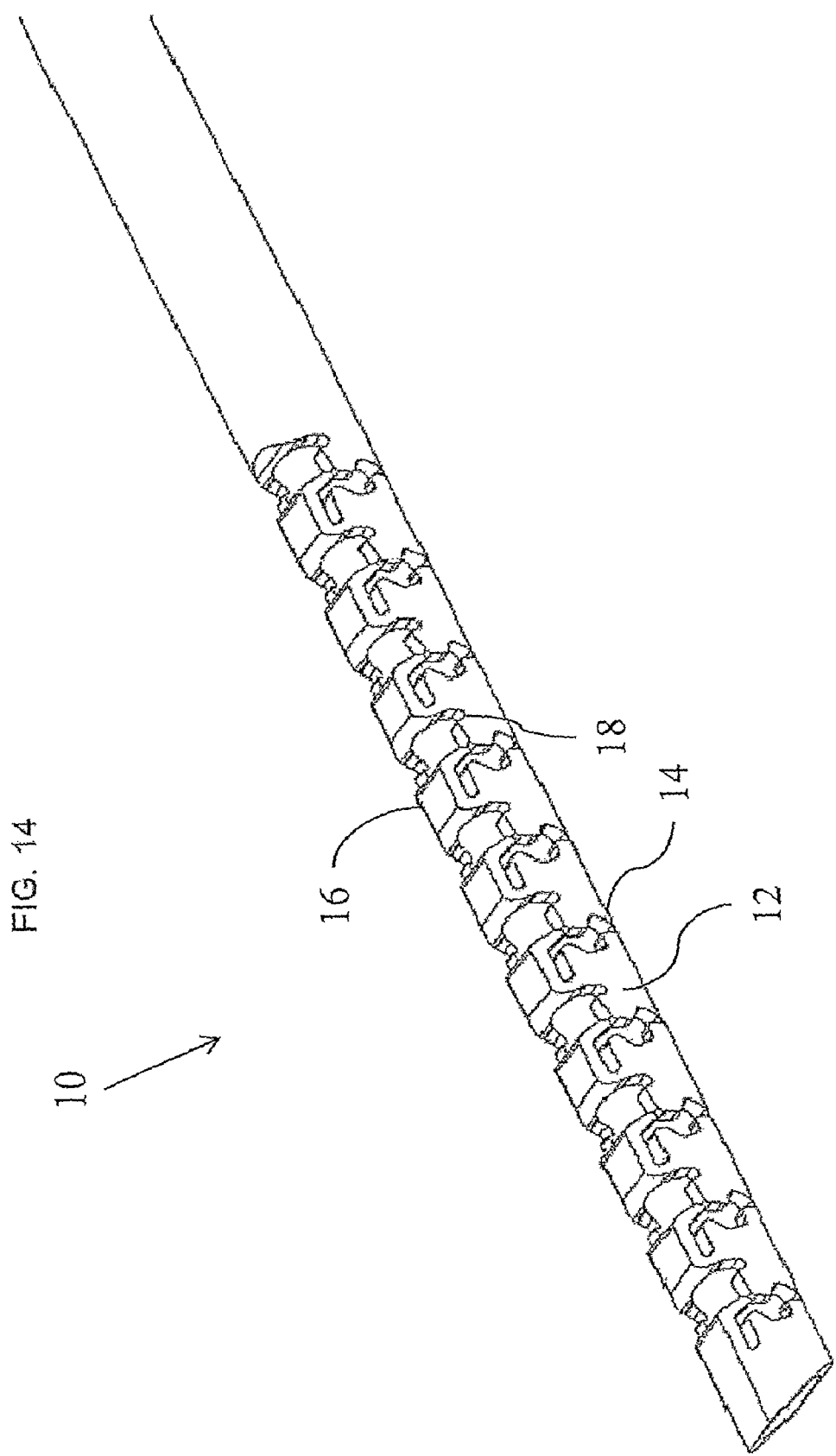
FIGS. 14-16 are two isometric views and one side view, respectively, of an alternative implementation of the elongated element of FIGS. 1-8 in which the elongated element is hollow.
Figure 15:
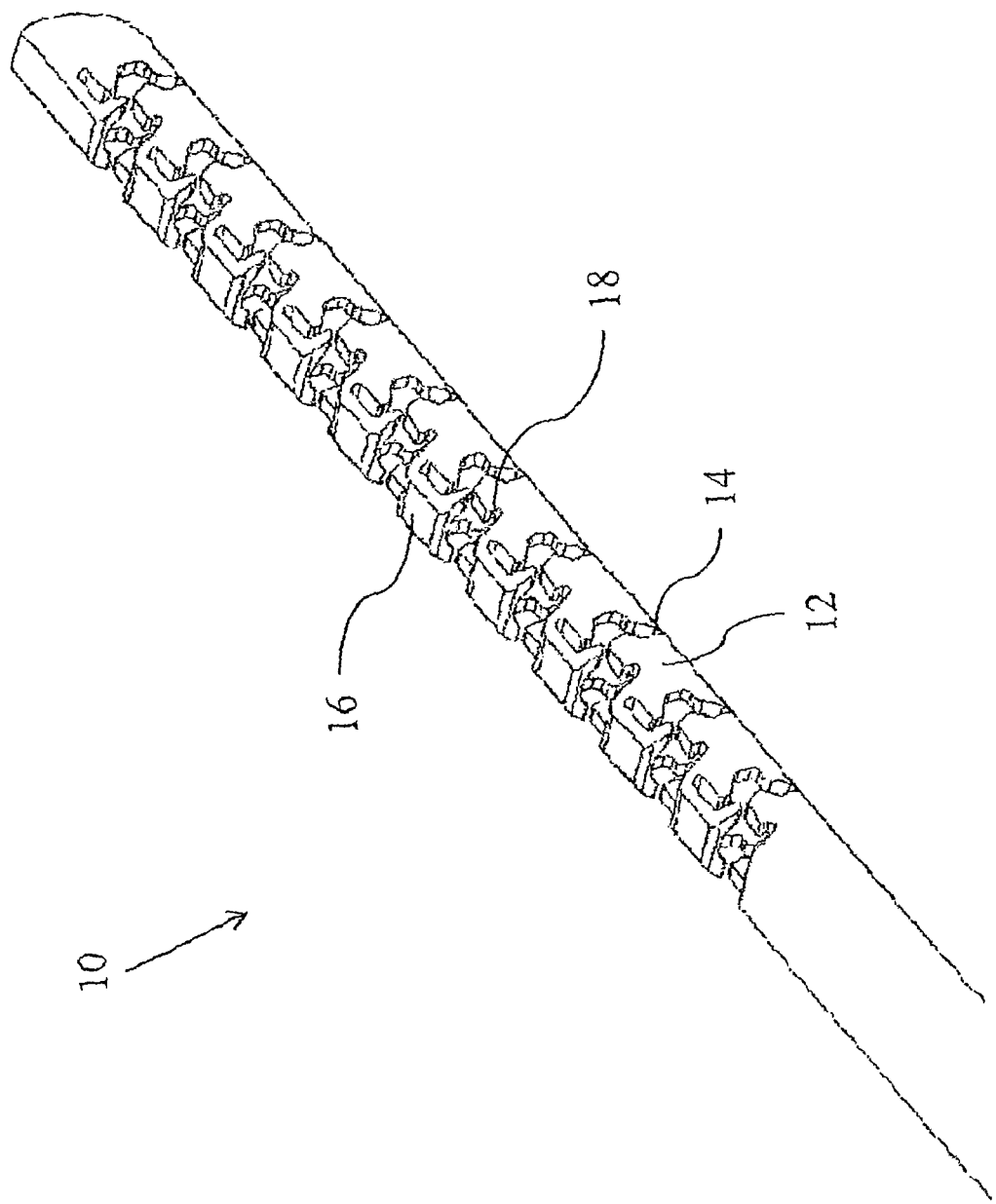
Figure 16:
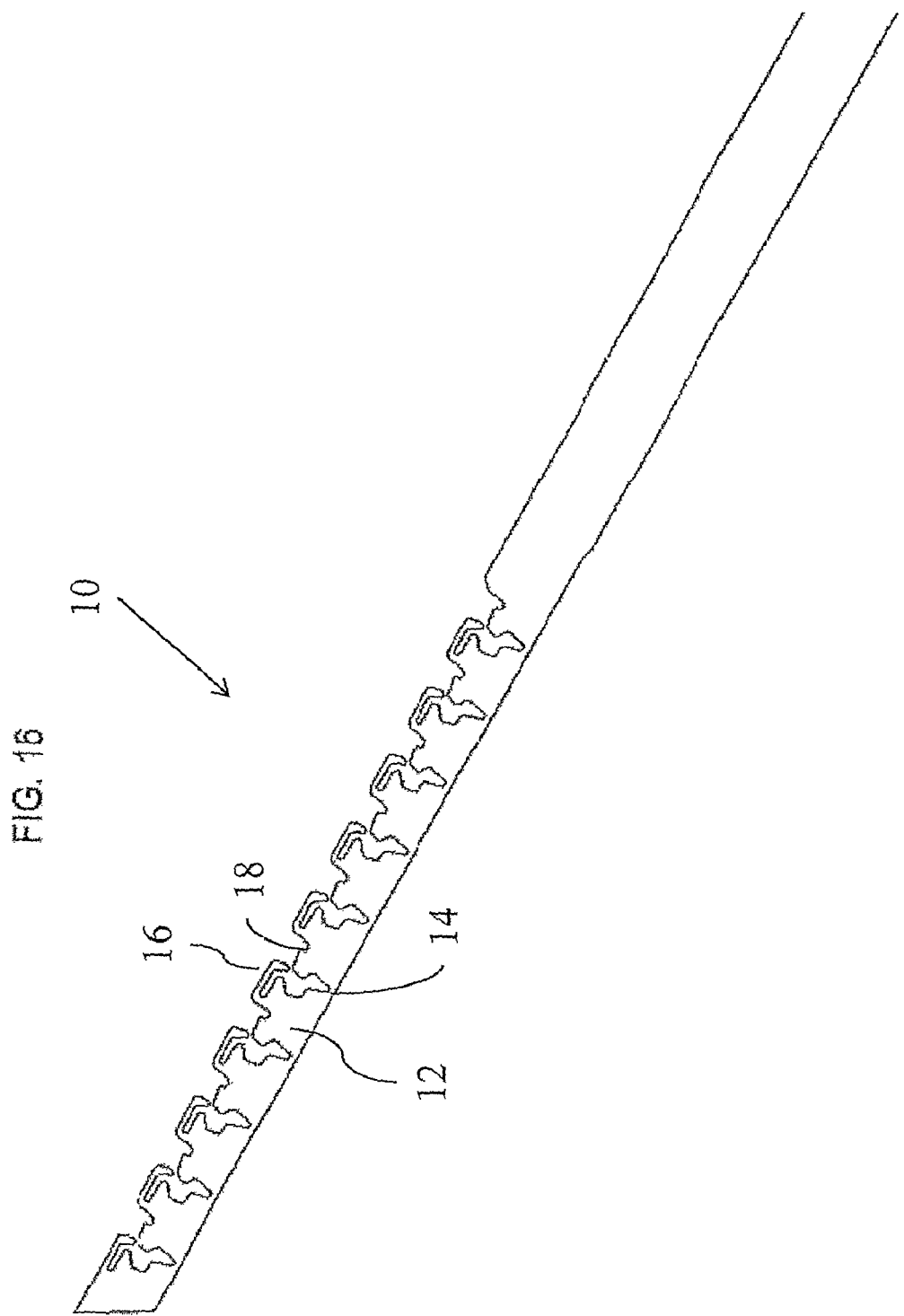
Figure 17:
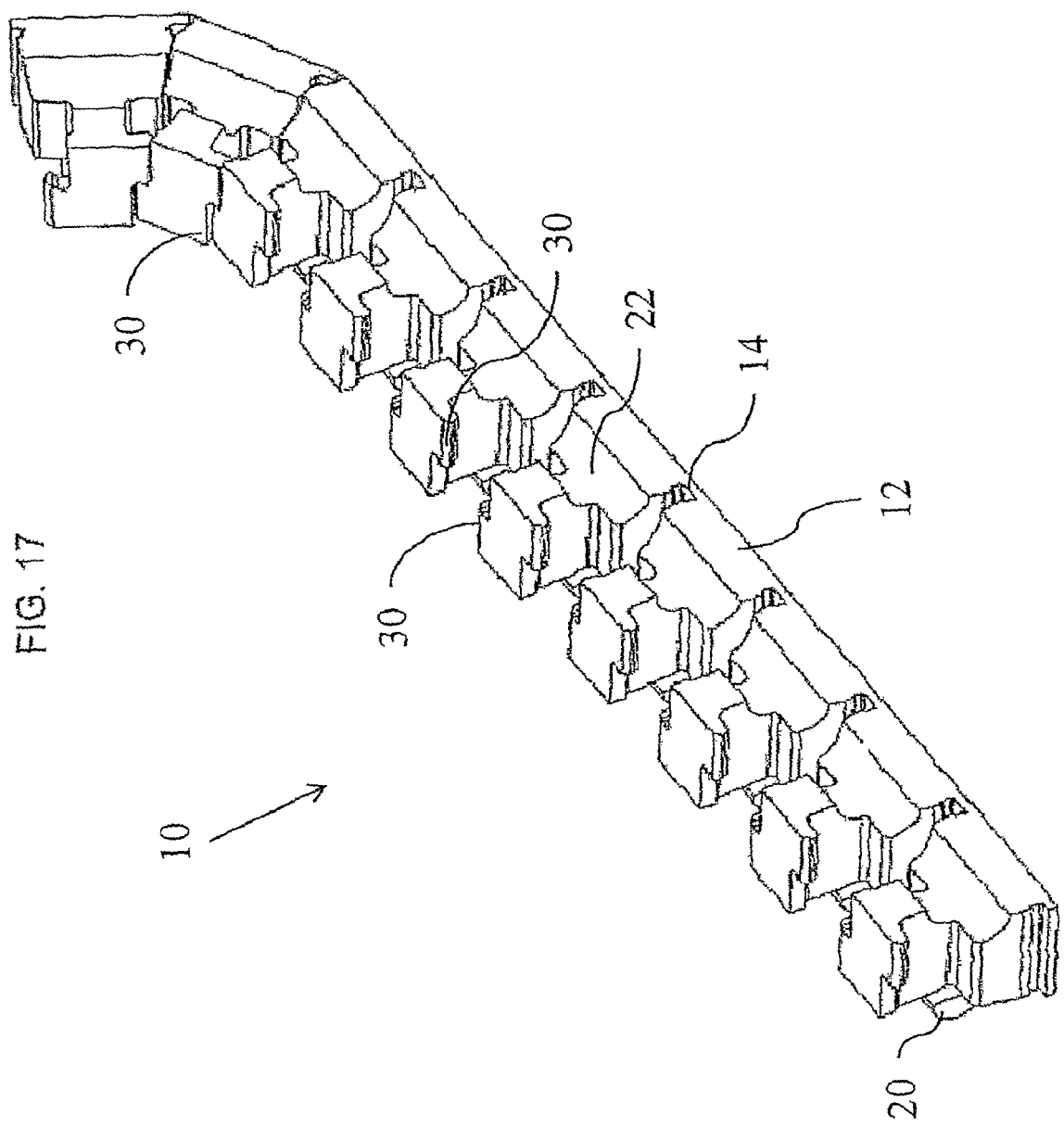
FIGS. 17-20 are various isometric views of a further embodiment of an elongated element, constructed and operative according to the teachings of the present invention, illustrating an alternative non-limiting example of an inter-segment locking configuration.
Figure 18:
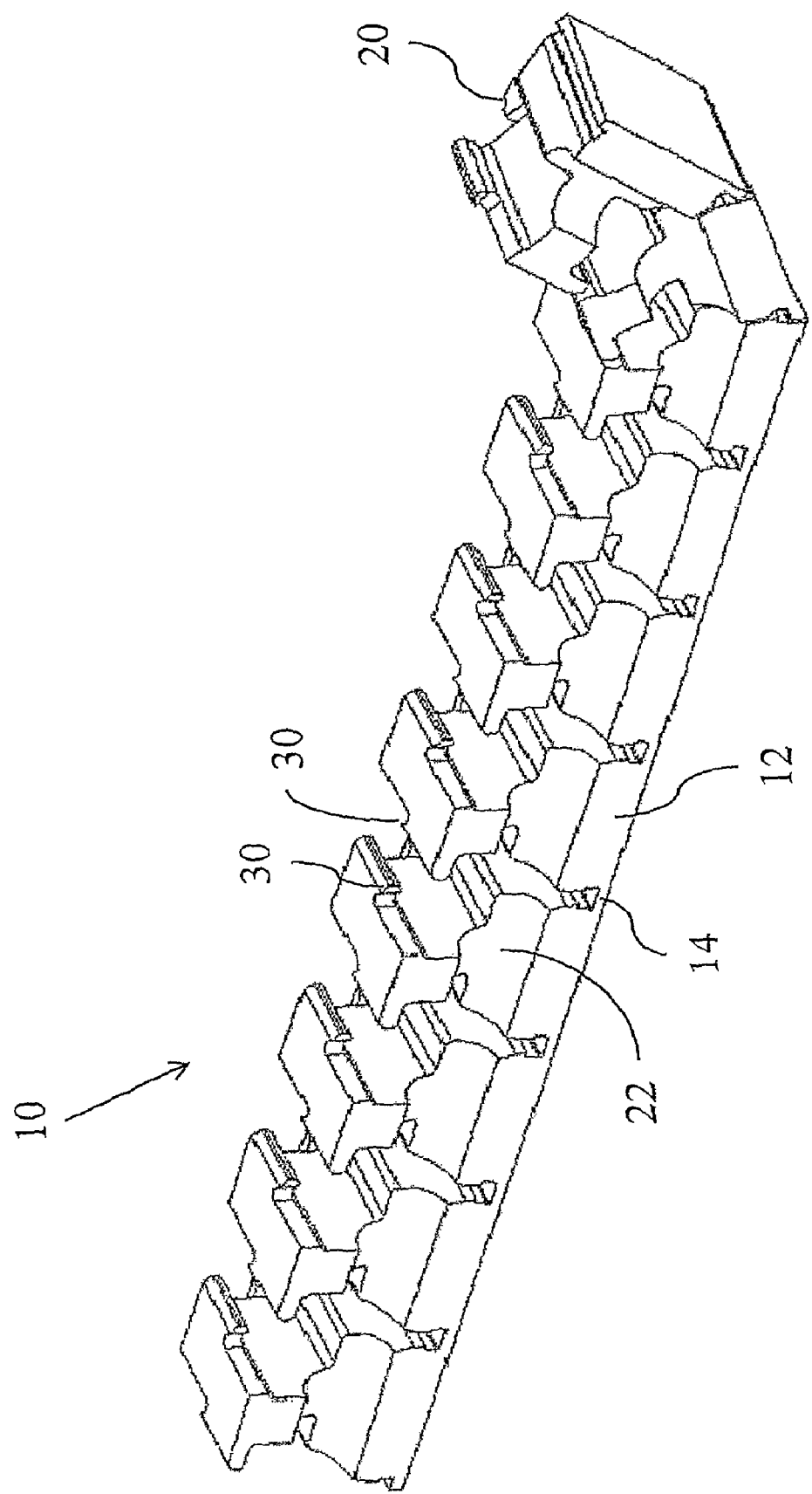
Figure 19:
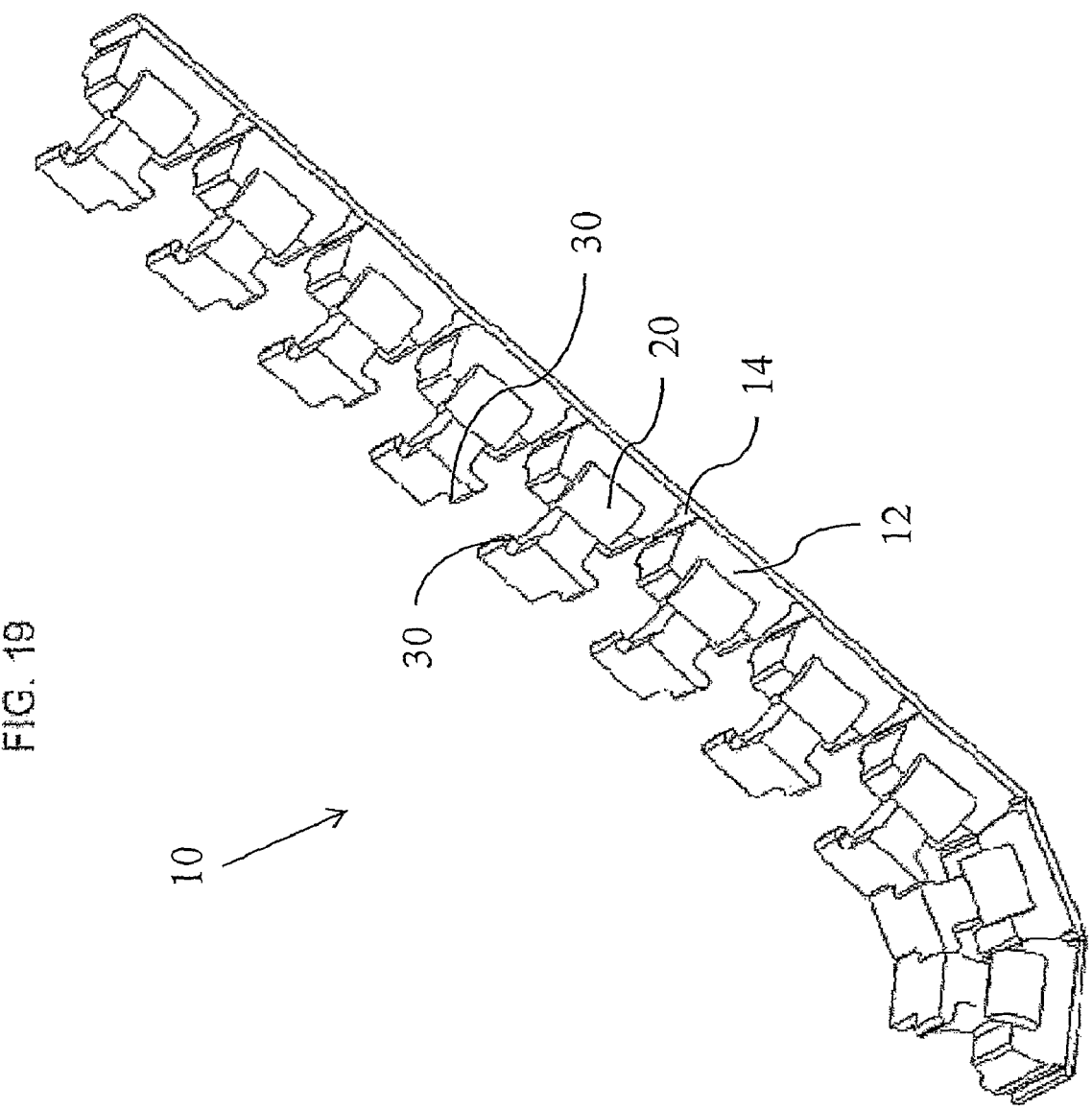
Figure 20:
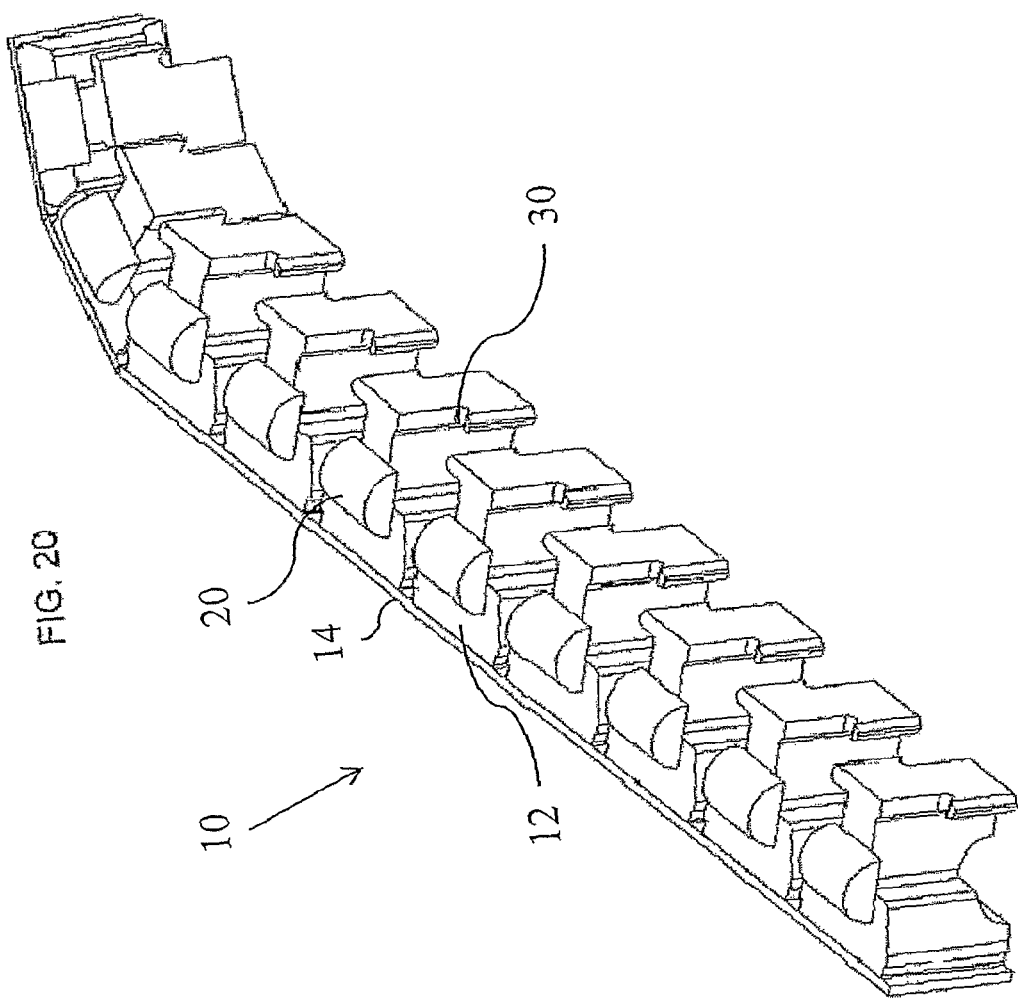
Figure 21:
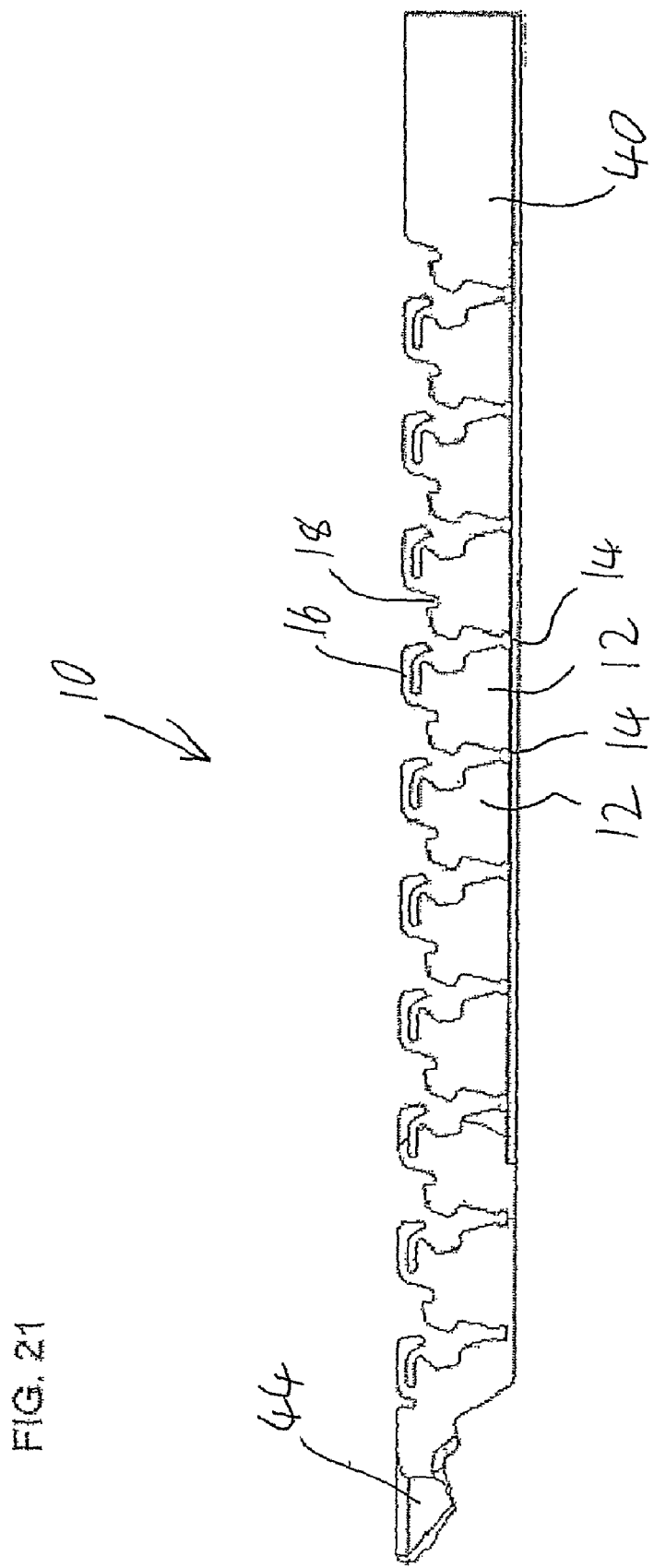
FIGS. 21-25 are various views of a further embodiment of the present invention including a loop-lock configuration for forming and maintaining the elongated element into a closed loop structure.

It should be noted that the elongated element may have any cross-sectional shape, and may be solid or hollow. By way of one additional non-limiting example, FIGS. 14-16 illustrate an elongated element generally analogous to that of FIGS. 1-8, but which is hollow. In this case, projecting spring elements 16 and cooperating recesses 18 are preferably implemented as a pair of spring elements, or a forked spring element 16, and a pair of recesses 18 per segment 12, formed using the wall thickness of the hollow structure.

Figure 35:
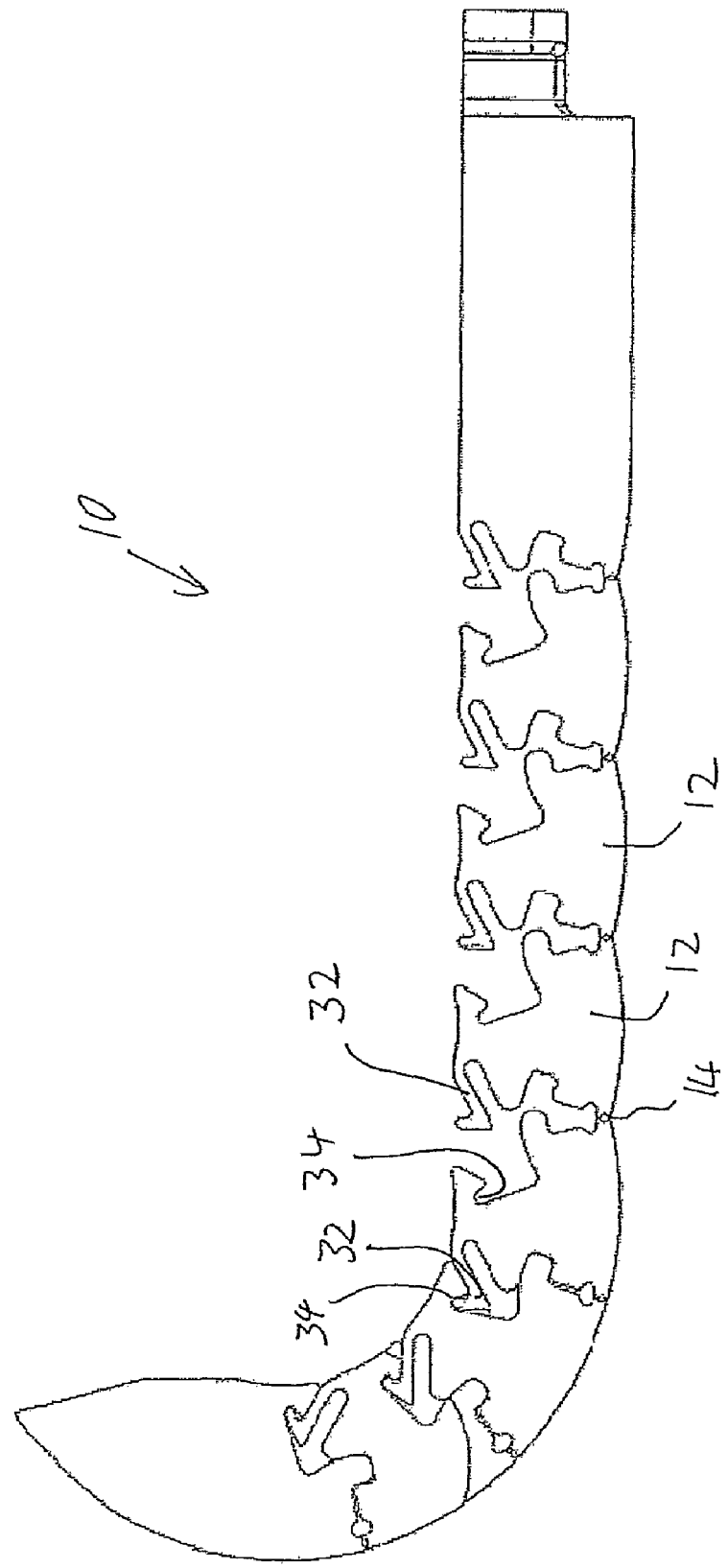
FIGS. 35 and 36 are views of an alternative implementation of an elongated element, constructed and operative according to the teachings of the present invention, illustrating an alternative non-limiting example of an inter-segment locking configuration.
Figure 36:
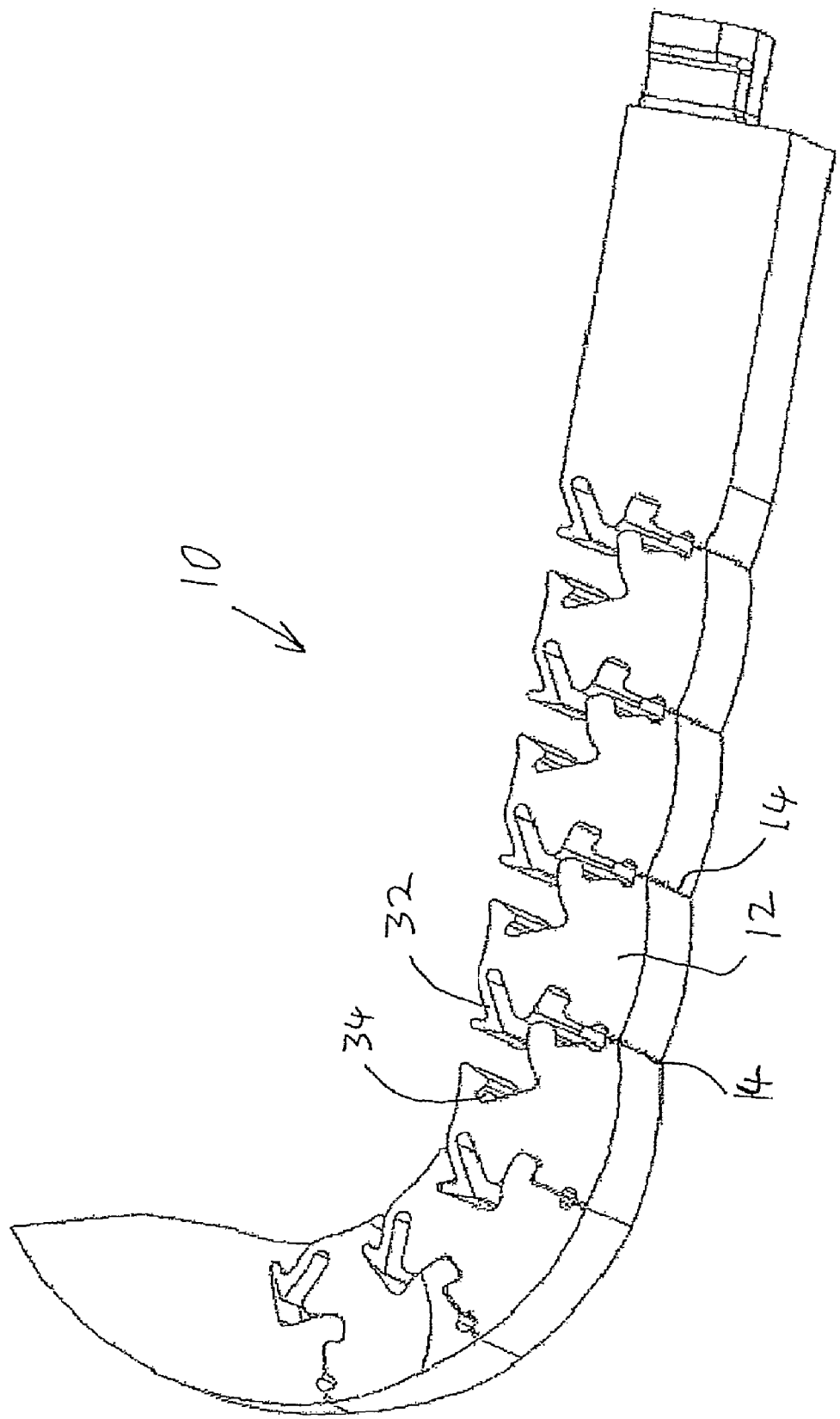

It should also be noted that the present invention is not limited to the specific locking configuration described above, and may be implemented with a wide range of locking configurations. By way of one additional non-limiting example, FIGS. 17-20 show an alternative implementation in which adjacent segments 12 interlock by engagement of complementary undercut shapes 30. In the embodiment shown, interlocking occurs through slight lateral flexing between adjacent segments 12. The flexibility required for this lateral flexing is provided by the effective hinges 14 between adjacent segments, here implemented as a leaf-spring that allows the required small degree of torsion. According to a further option, illustrated in FIGS. 35 and 36, the locking configuration may be implemented internally, i.e., so that the resilient elements 32 achieving the locking effect are covered, or at least substantially contained, within the structure when closed. In the implementation illustrated here, the resilient locking features are biased away from the effective hinges 14 between the segments and selectively engage under a correspondingly formed recess or ledge 34.

As mentioned earlier, the effective hinges 14 for all of the embodiments illustrated herein may be implemented in a wide range of ways, whether integral to segments 12 themselves (e.g., with the entire element formed from an elongated rod cut out appropriately) or formed from a separate structure ("backbone") to which the individual segments 12 are attached. In the latter case, the backbone may be of a different material from the segments themselves, chosen according to the intended application. Options for materials for the backbone include, but are not limited to, metallic materials, various plastics and other polymers, and fabrics.

Turning now to the second aspect of the present invention, illustrated with reference to FIGS. 21-34, it is a particular feature of certain preferred devices according to the present invention that the device includes a loop-lock configuration for securing the elongated element into a closed loop. In this case, a leading portion and a rear portion of elongated element 10 typically include features forming at least part of the loop-lock configuration. Alternatively, or additionally, part of the loop-lock configuration may be provided by features of the delivery conduit. The loop-lock configuration thus forms a mechanically stable closed loop structure which is useful in a wide range of applications.

Figure 22:
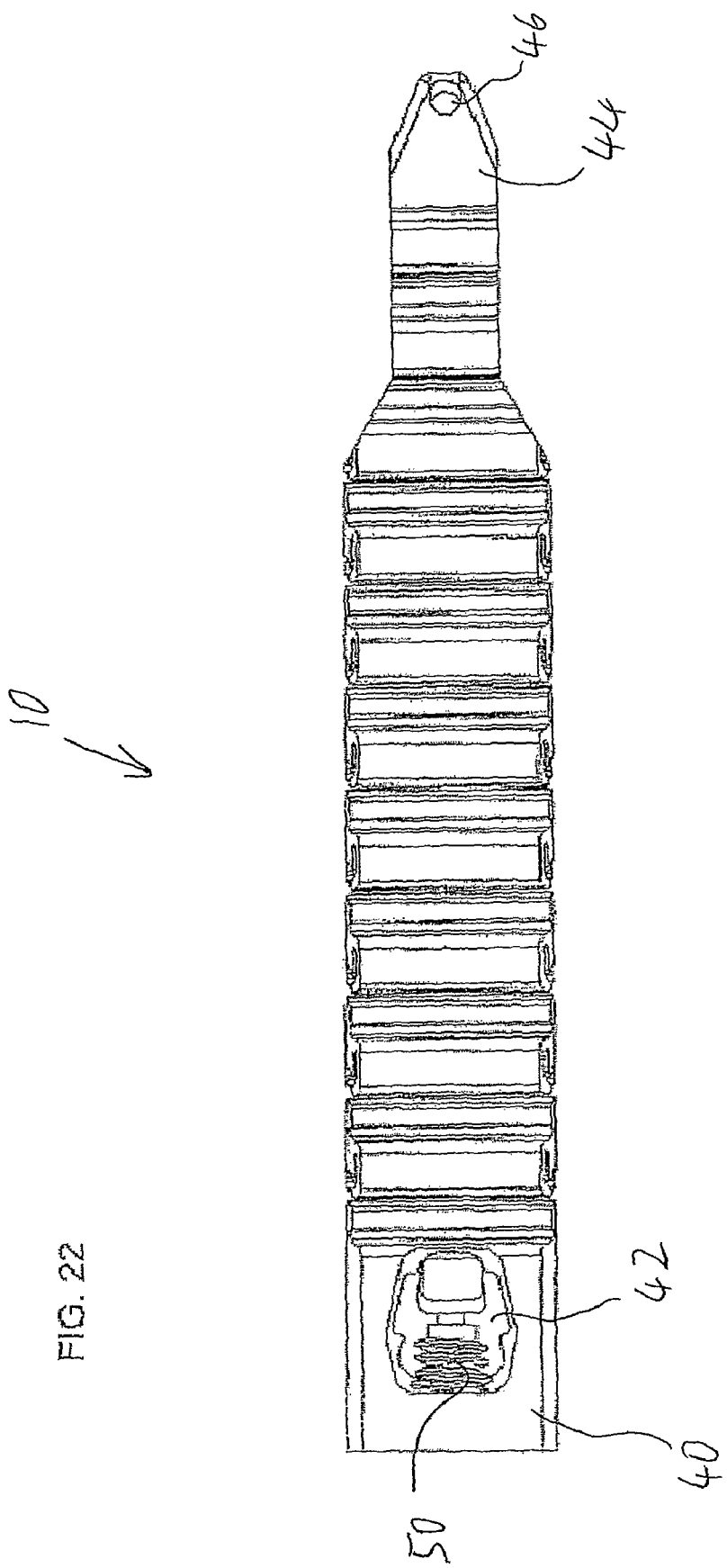
Figure 23:
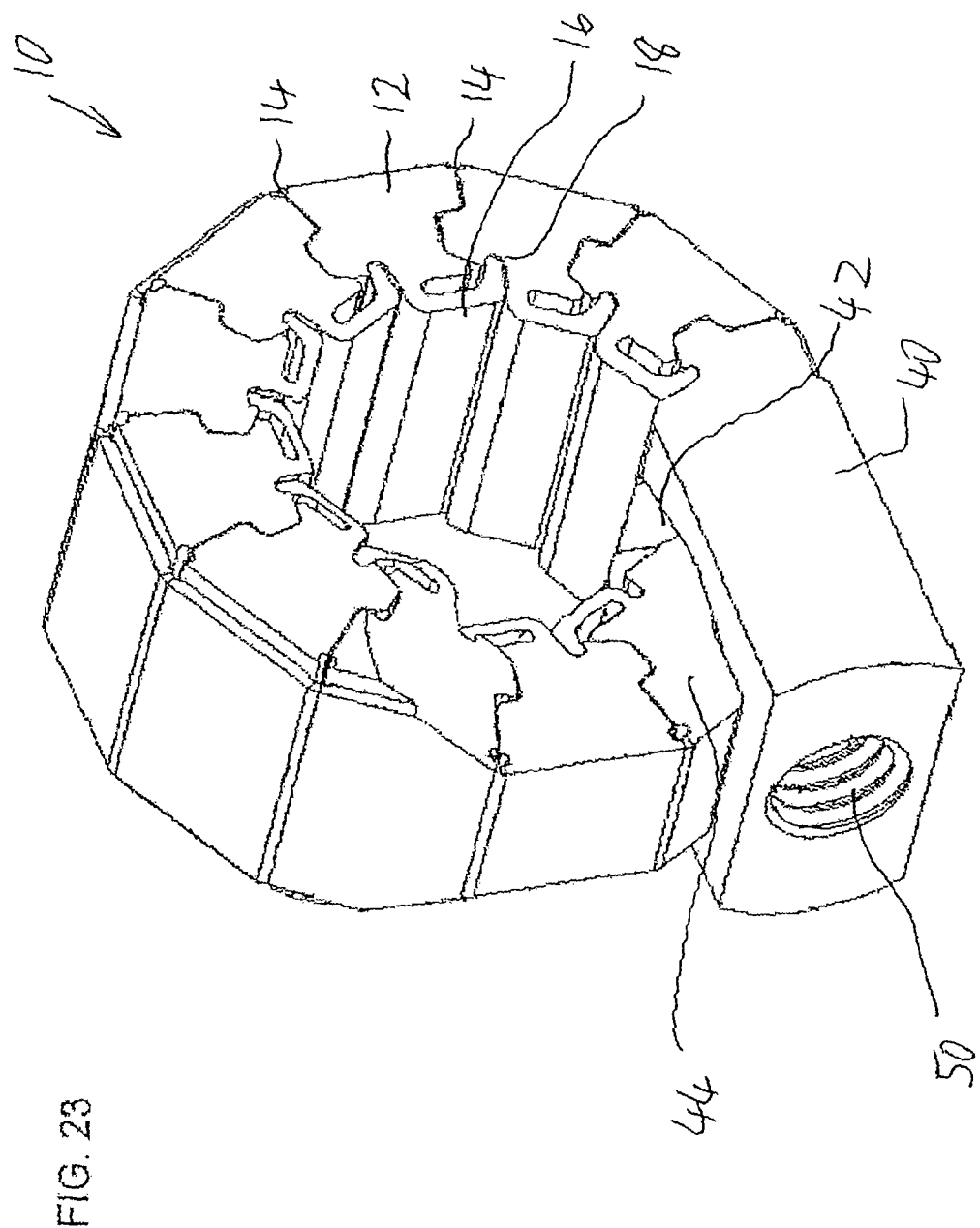
Figure 24:
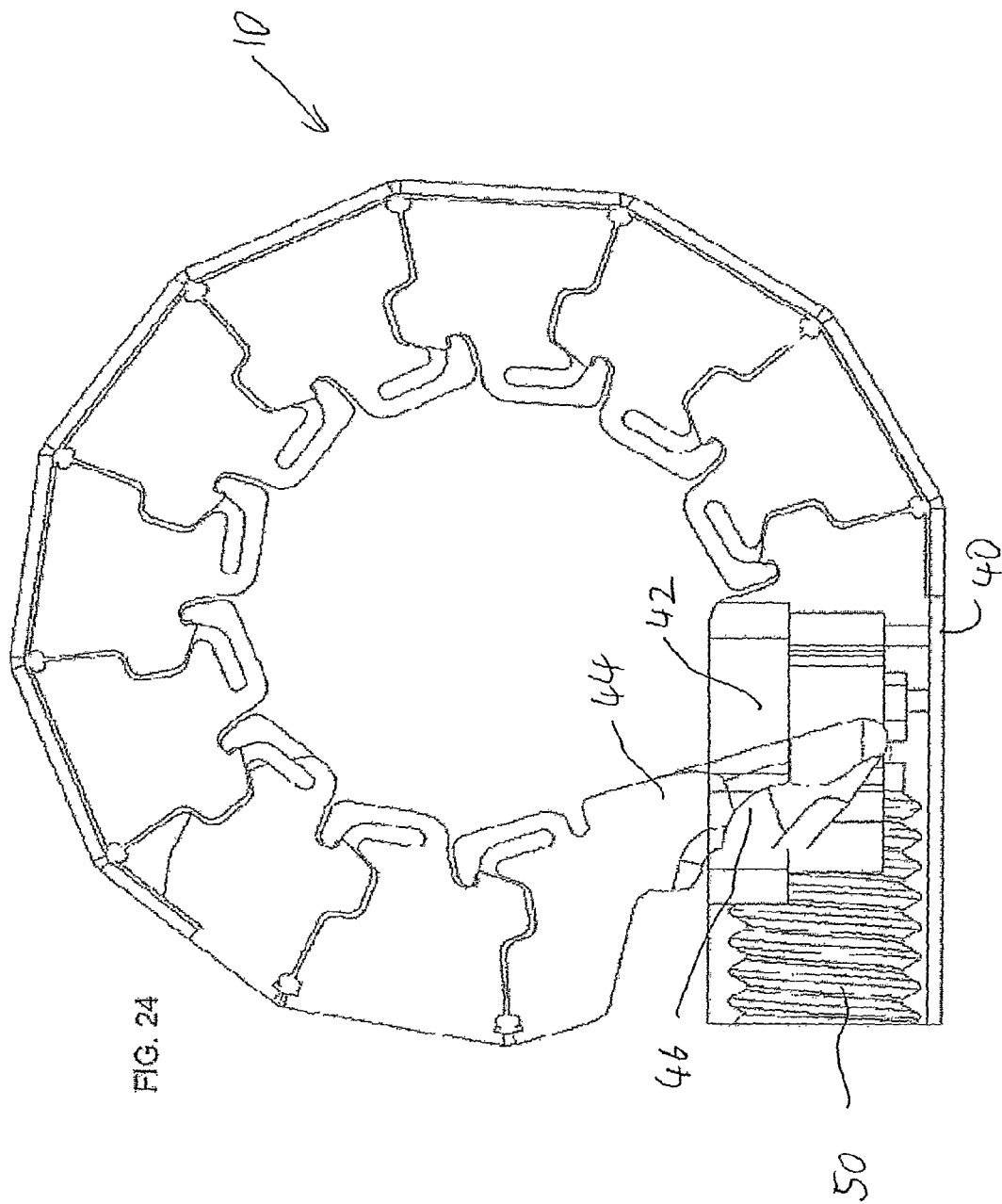
Figure 25:
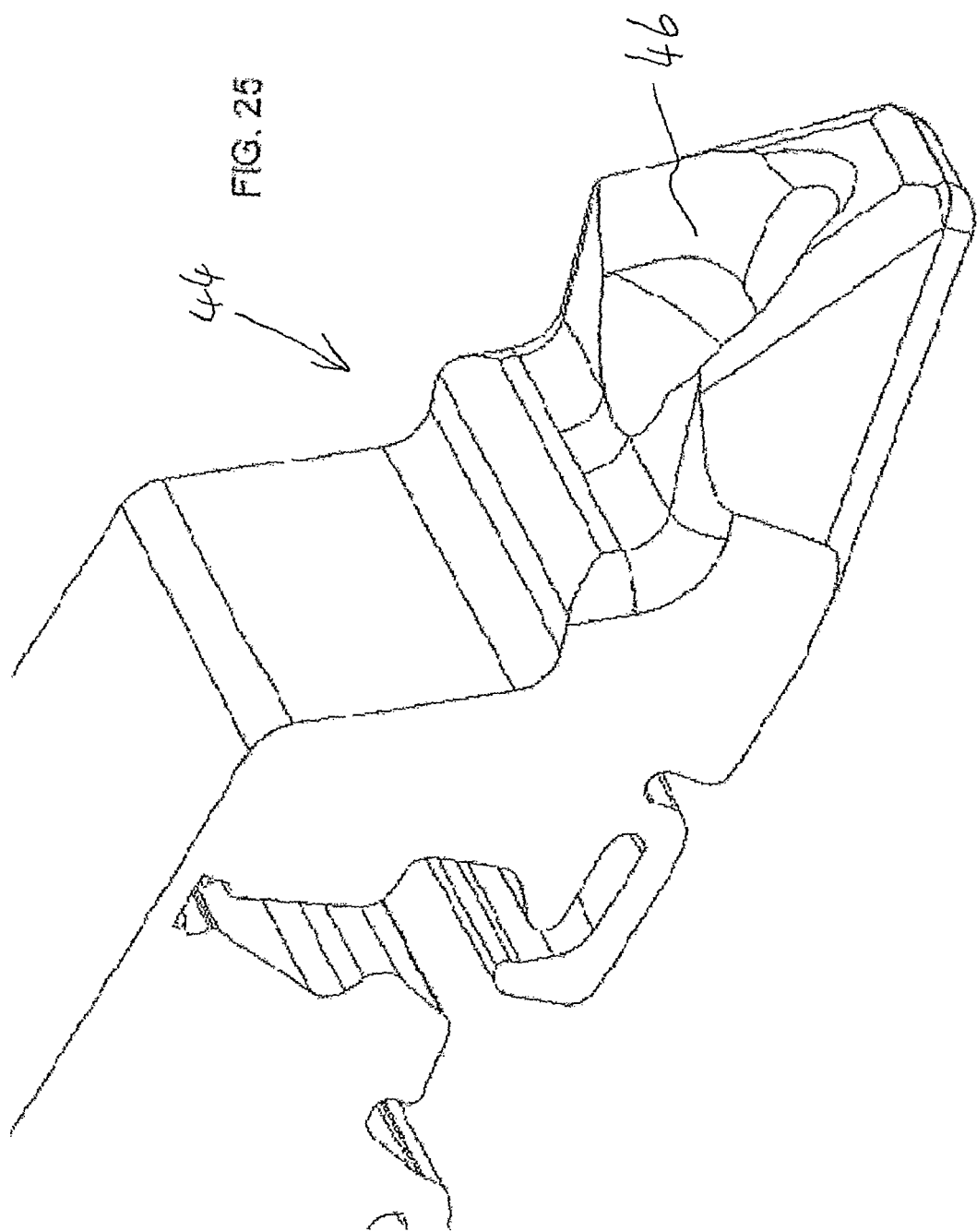

A first implementation of a loop-lock configuration is illustrated in FIGS. 21-27. In this case, a rear (i.e., later deployed) part 40 of elongated element 10 is formed with a shaped upper recess or cavity 42 for receiving at least part of the leading portion 44. As best seen in FIG. 22, rear portion 40 and its cavity 42 have a width greater than that of leading portion 44 so that the leading portion can be accommodated within the cavity. In the example illustrated here, this is implemented by forming a number of segments 12 closest to the tip of elongated element with a narrower cross-section.

Figure 26:
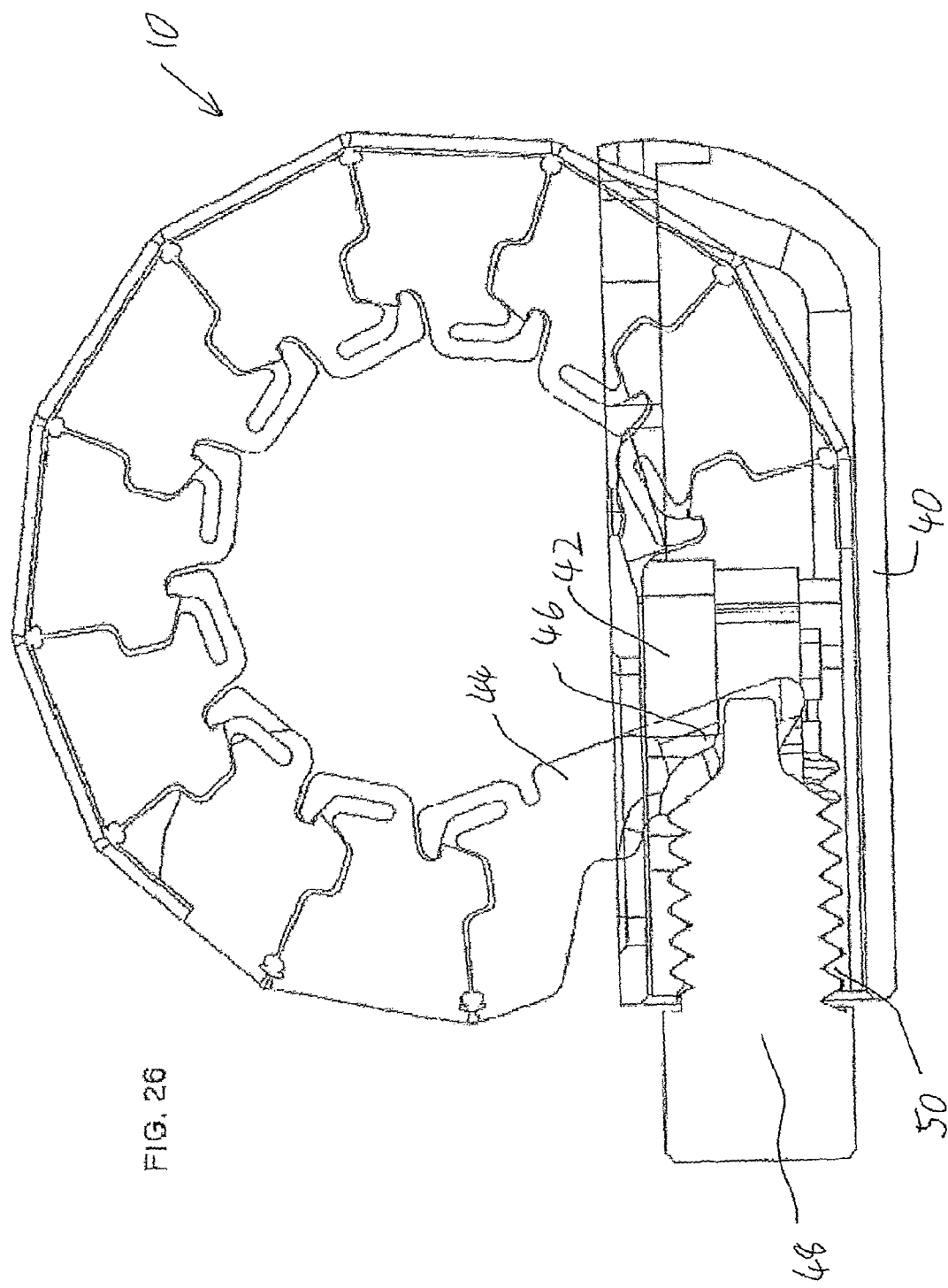
FIGS. 26 and 27 are additional views showing the loop-lock configuration of FIGS. 21-25 together with a delivery conduit that forms part of the loop-lock configuration.
Figure 27:
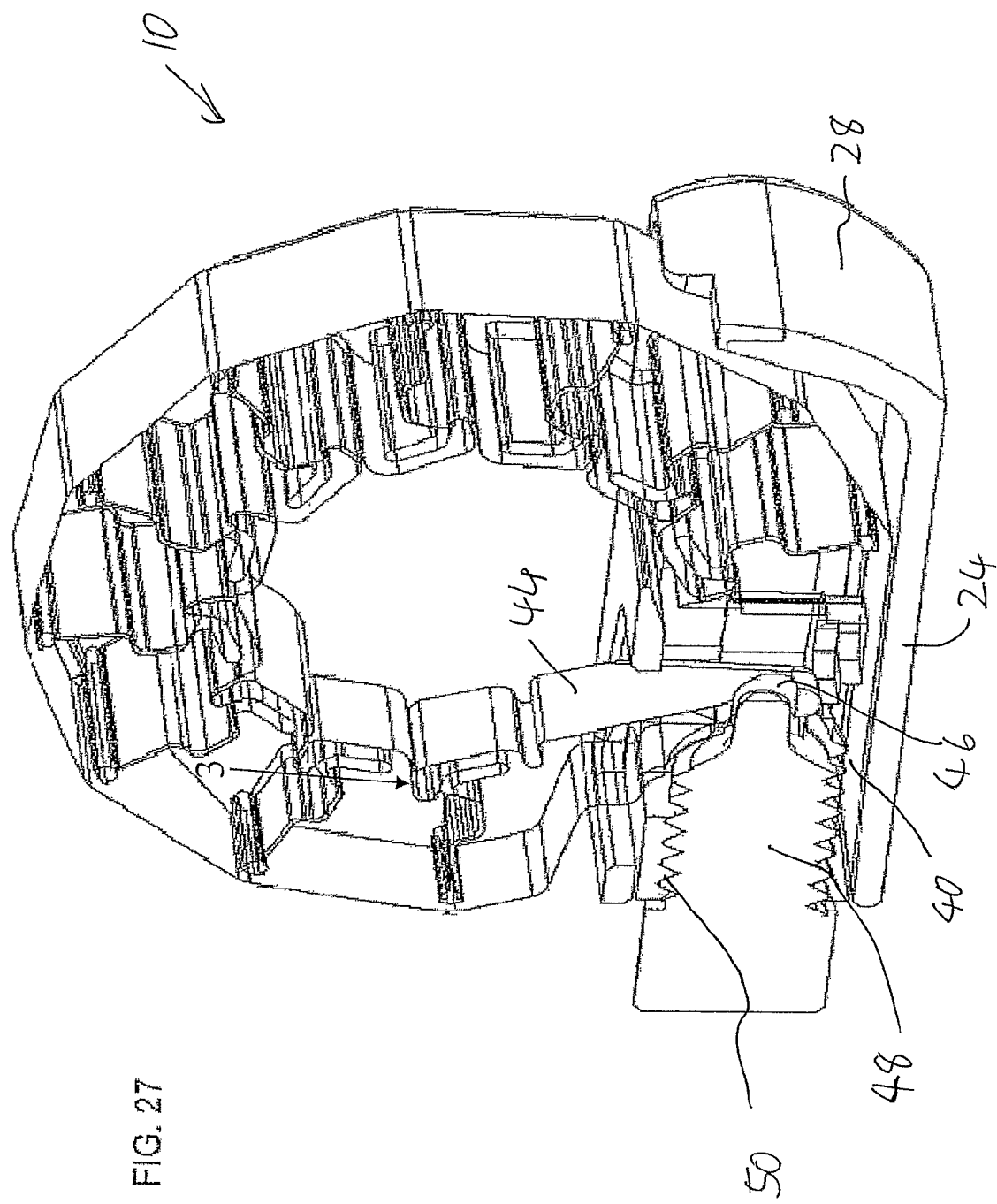

Leading portion 44 preferably includes a shaped recess 46 (best seen in FIG. 25) which is configured to be engaged by an elongated locking element 48. As shown in FIGS. 26 and 27, in the preferred implementation illustrated here, elongated locking element 48 is a threaded element (e.g., a bolt) received in a complementary threaded bore 50 formed in rear portion 40. Bore 50 intersects with cavity 42 and is aligned to engage shaped recess 46 so as to achieve locking of the closed-loop structure. In the particularly preferred implementation shown here, bore 50 is a rearward-opening bore accessible from the feed direction of the elongated element.

In use, as the elongated element is advanced and changes from its initial straightened state (FIGS. 21-22) to its arcuate state (FIGS. 23-24), leading portion 44 enters the shaped upper cavity 42 as shown. FIGS. 26 and 27 show elongated element 10 together with a delivery conduit 24 as described above. Once leading portion 44 reaches its position inserted into the shaped upper cavity 42, threaded bolt 48 is inserted into rearward opening threaded bore 50 and tightened, thereby bearing on the shaped recess 46 of leading portion 44 and locking it in a closed-loop configuration. Optionally, shaped recess 46 may be implemented as a through-bore and bolt 48 with a corresponding axial projection, thereby providing positive engagement of the tip within the recess as illustrated in FIGS. 26 and 27.

Figure 28:
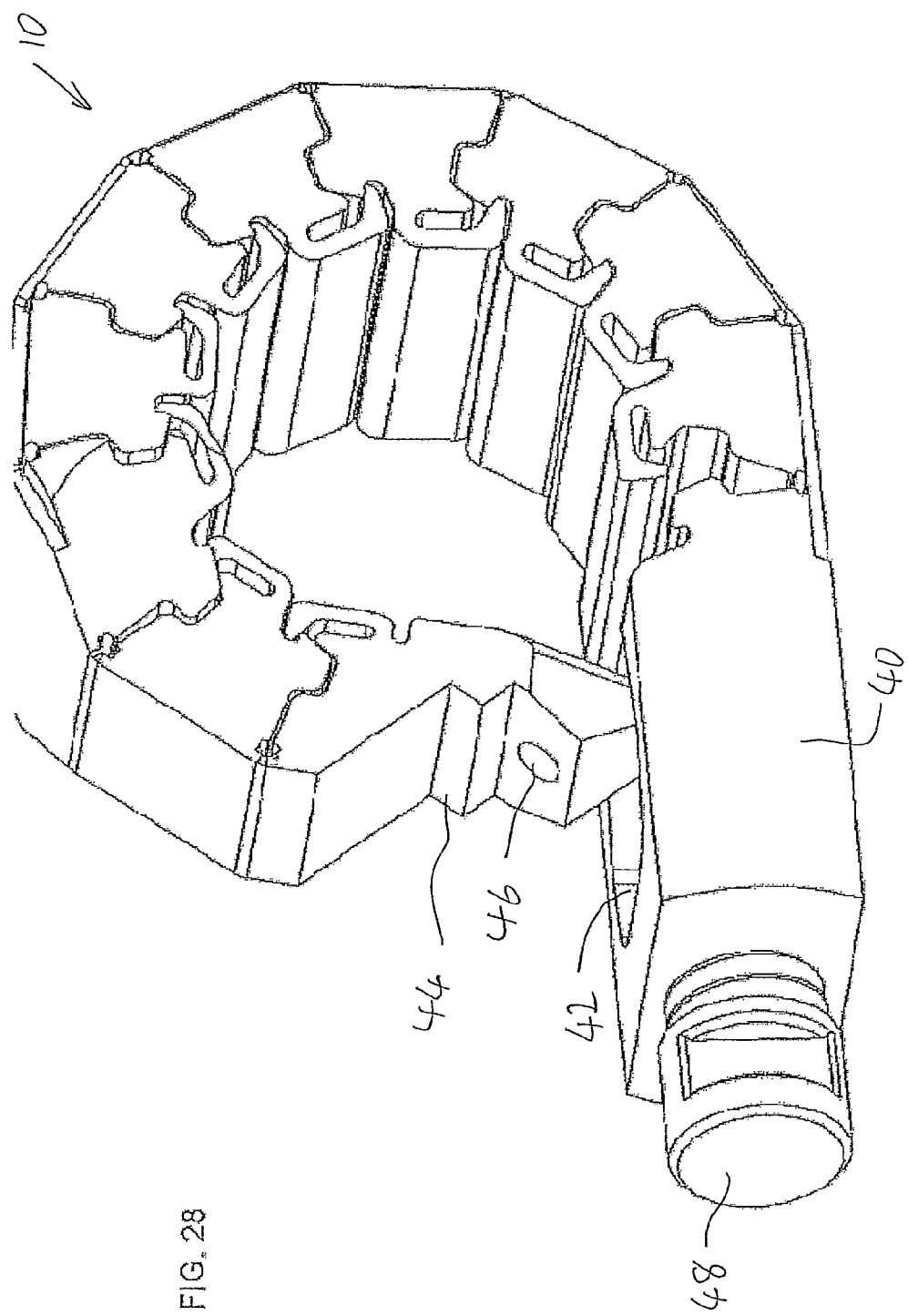
FIGS. 28-30 are various views showing a first variant of the loop-lock configuration of FIGS. 21-27.
Figure 29:
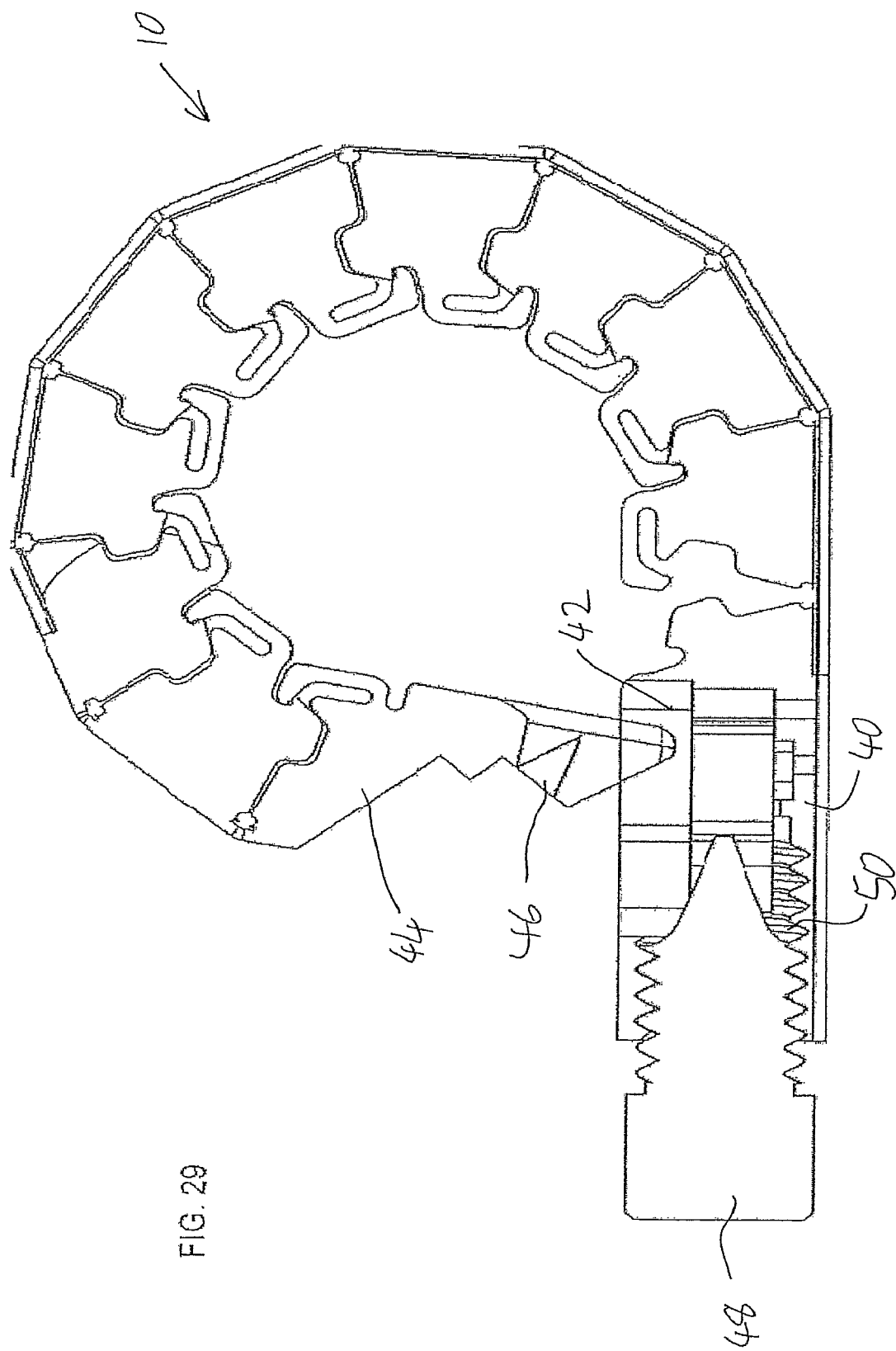
Figure 30:
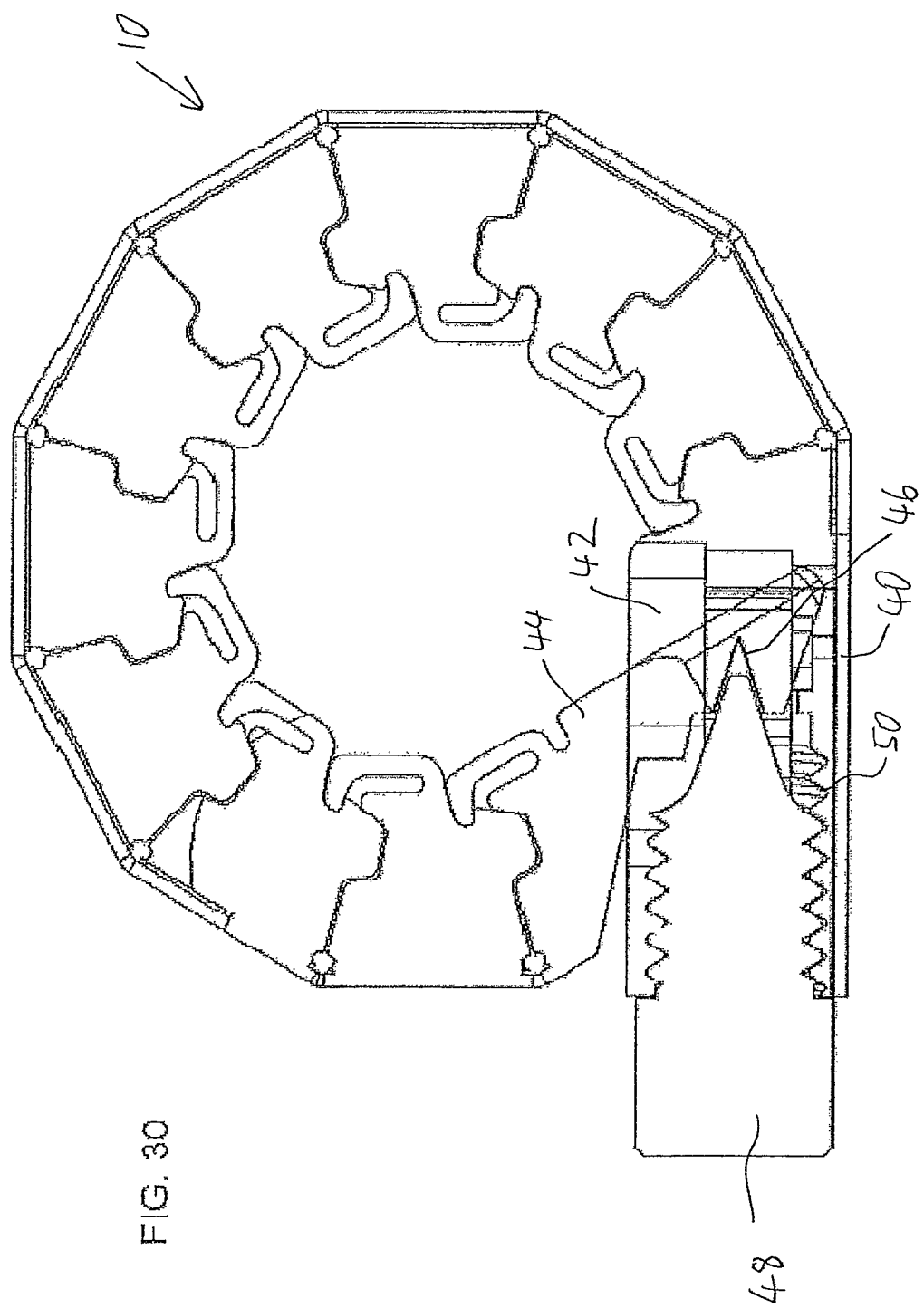
Figure 31:
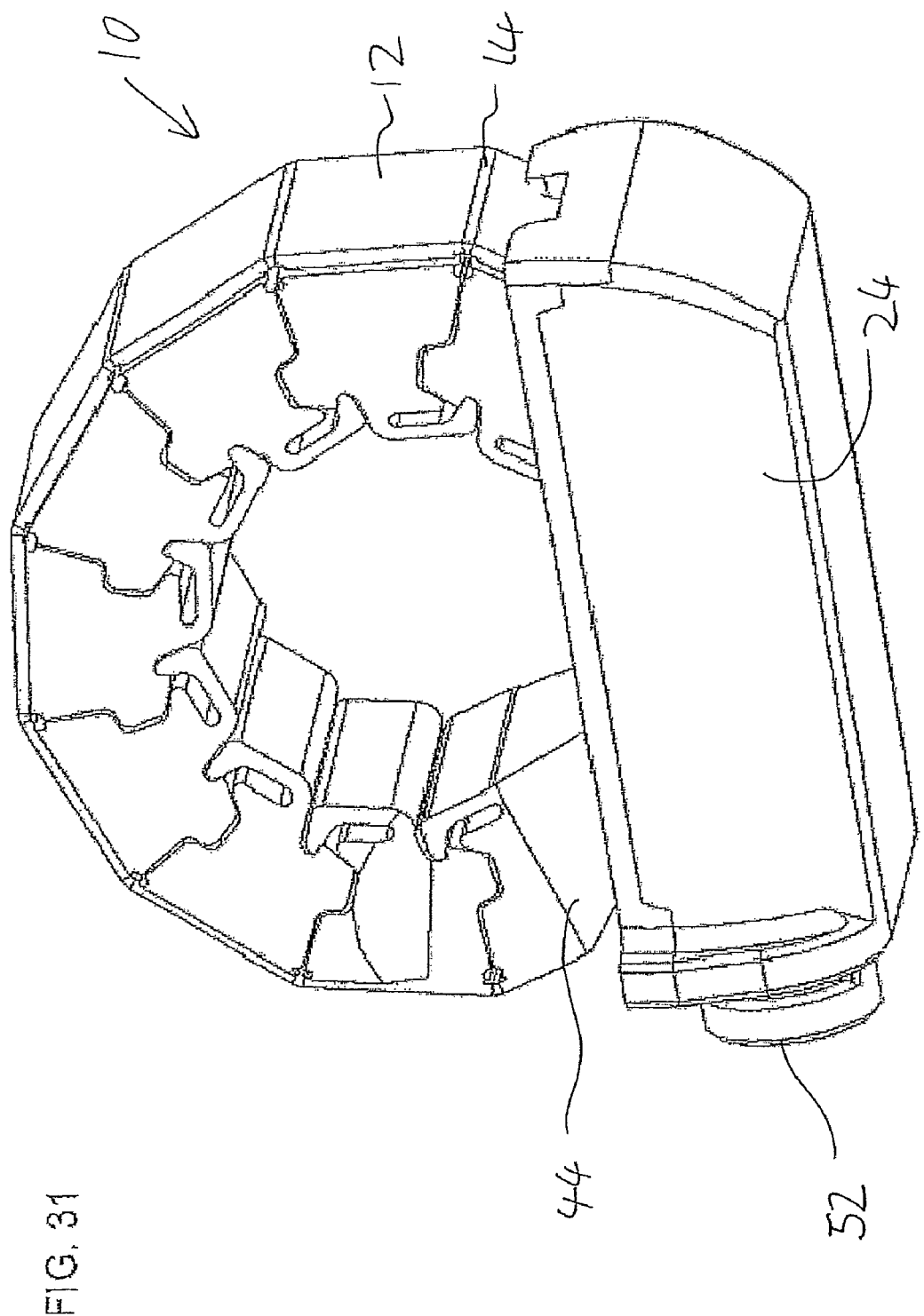
FIGS. 31-34 are various views showing a second variant of the loop-lock configuration of FIGS. 21-27.
Figure 32:
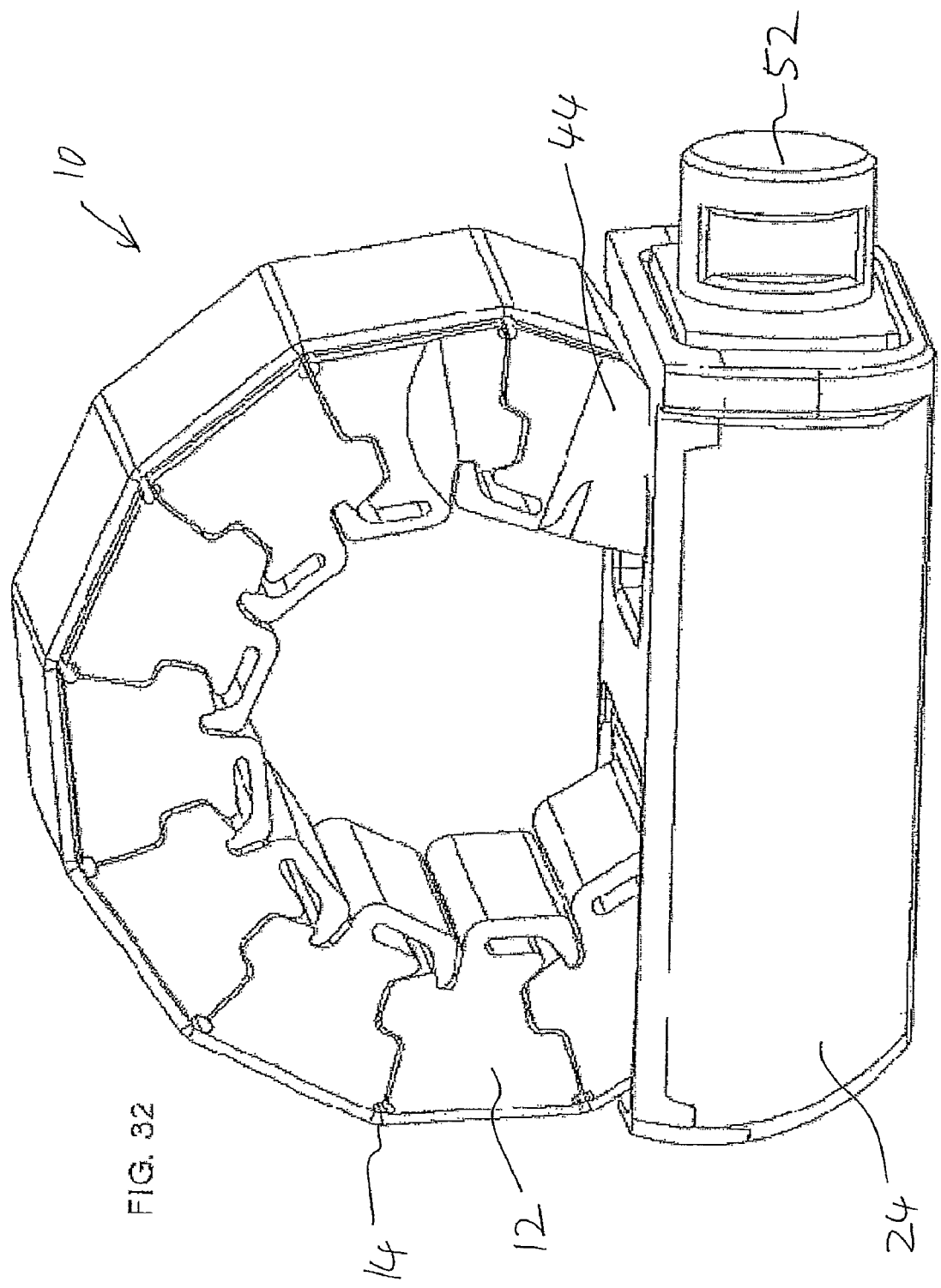

FIGS. 28-30 illustrate an embodiment that is essentially similar to that of FIGS. 21-27 but employs a conical-tipped bolt 48 as the locking element engaging a corresponding conical recess 46 without a through-bore. In other respects, the structure and operation of this embodiment is equivalent to that of FIG. 21-27 above.

Figure 33:
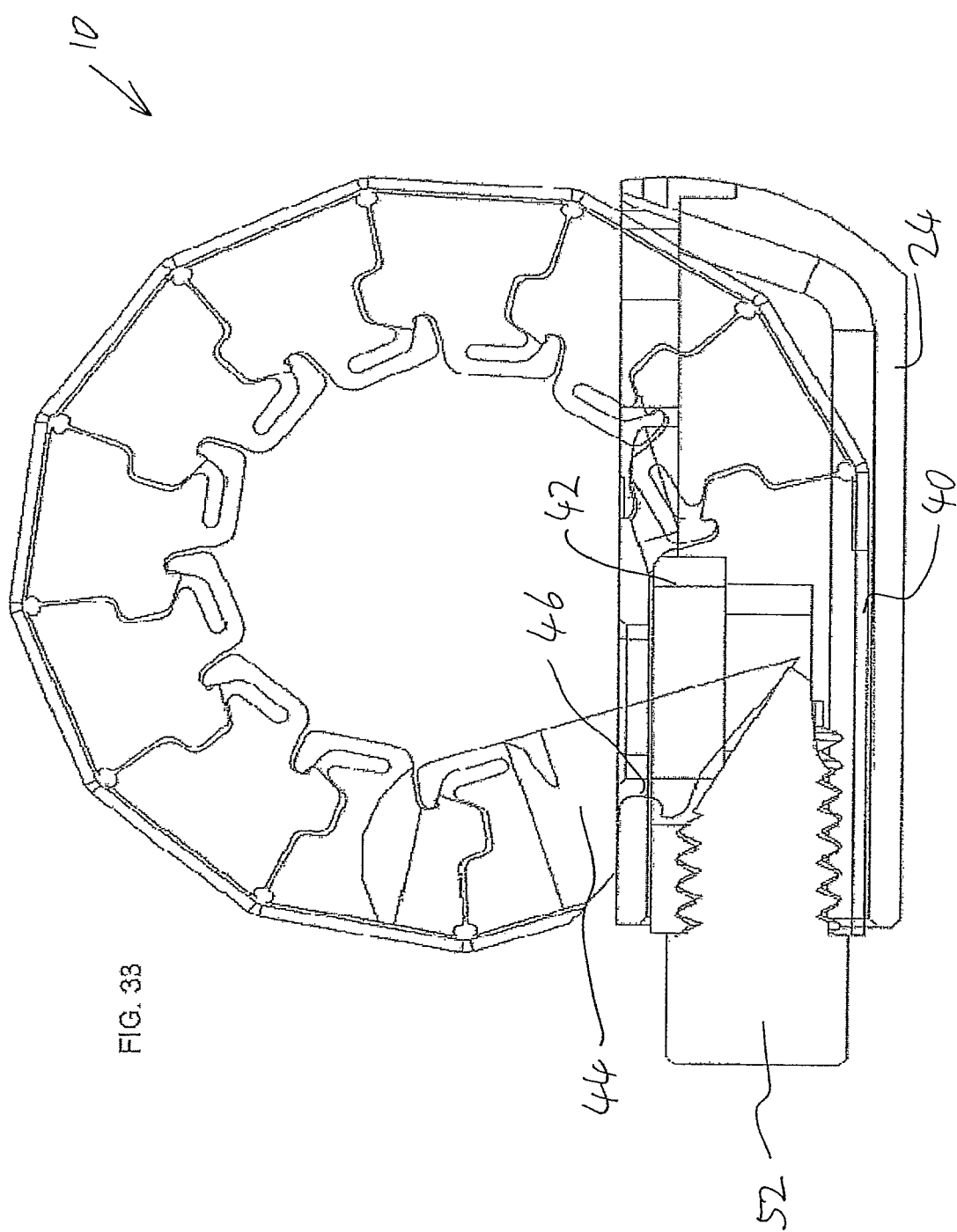
Figure 34:
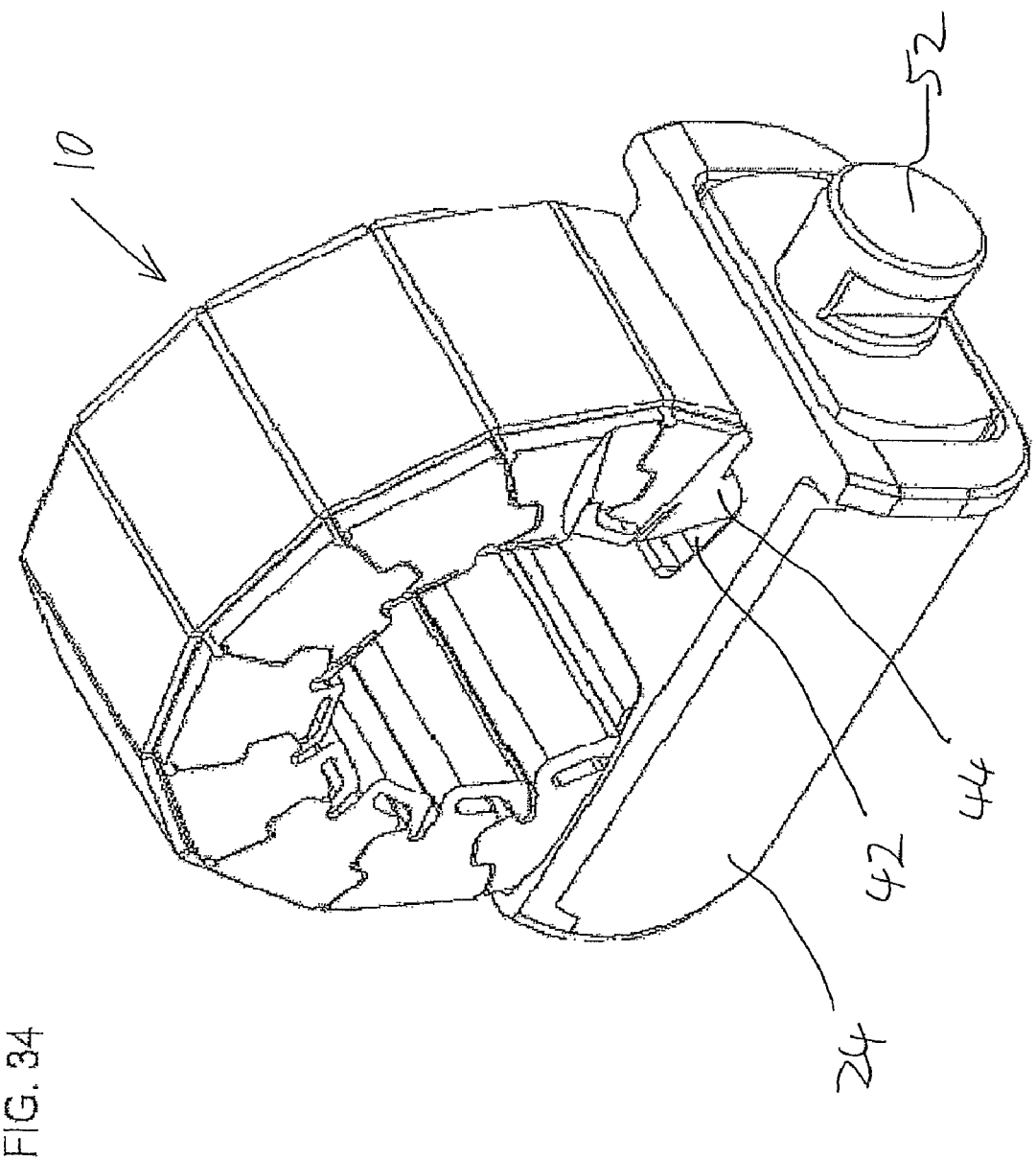

FIGS. 31-34 show an alternative approach to the loop-lock configuration in which shaped recess 46 is implemented as a side-to-side channel in leading portion 44. In this case, leading portion 44 is preferably configured to engage either a suitably shaped edge of cavity 42 or, as in the case illustrated here, a static ridge formed in the delivery conduit 24 as best seen in FIG. 33. The engagement configuration provided by the side-to-side channel is preferably analogous to a barbed shape, facilitating initial engagement and retention of the device in its closed-loop state when leading portion 44 reaches the appropriate position. Optionally, a rotatable pin element 52 (also seen in FIG. 33) provides a cam-like release mechanism that allows disengagement of the tip in the case that the device is to be removed.

It will be appreciated that the above descriptions are intended only to serve as examples, and that many other embodiments are possible within the scope of the present invention as defined in the appended claims.

What is claimed is:

1. A device for forming closed loop structures comprising an elongated element formed from a plurality of segments sequentially interconnected so as to form an effective hinge between adjacent of said segments, said segments and said effective hinges being configured such that said effective hinges allow deflection of each segment relative to adjacent segments between a reduced-curvature state and a flexed state,
wherein a rear portion of said elongated element includes a recess, and wherein a leading portion of said elongated element and said recess are configured so that at least part of said leading portion is received within said recess when said elongated element is in said flexed state so as to form a closed loop structure.

2. The device of claim 1, wherein said leading portion has a first width measured parallel to said effective hinge and said rear portion has a second width measured parallel to said effective hinge, said second width being greater than said first width.

3. The device of claim 1, wherein said leading portion is configured to engage an edge of said recess.

4. The device of claim 1, wherein rear portion further includes a rearward extending bore contiguous with said recess, and wherein said leading portion includes a recess which forms a contiguous opening with said rearward extending bore when said elongated element is deployed as said closed loop structure.

5. The device of claim 4, further comprising an elongated locking element for insertion through said rearward extending bore to engage said shaped recess, thereby locking said closed loop structure.

6. The device of claim 5, wherein said elongated locking element and said bore are threaded.

7. The device of claim 5, wherein said bore is a rearward-opening bore.

8. The device of claim 1, wherein each of the effective hinges is formed by a flat connecting portion of flexible material interconnecting between adjacent of the segments.

9. The device of claim 8, wherein each of the flat connecting portions is integrally formed with adjacent of the segments.

10. The device of claim 8, wherein all of the segments and the flat connecting portions are integrally formed.

11. The device of claim 1, further comprising a delivery conduit having a passageway shaped to allow delivery of said elongated element along said passageway, said conduit including a lateral opening for accommodating at least part of said leading portion.

12. The device of claim 11, wherein said conduit includes at least one feature configured to engage part of said leading portion, thereby providing part of said loop-lock configuration.

13. The device of claim 1, wherein said leading portion and said rear portion of said elongated element include features forming at least part of a loop-lock configuration, said loop-lock configuration being operative to lock together said leading portion and said rear portion so as to lock said closed loop structure.

14. The device of claim 4, wherein said recess of said leading portion is implemented as a bore deployed to form a contiguous opening with said rearward extending bore when said elongated element is deployed as said closed loop structure.

* * * * *